United States Patent [19]
Cohn et al.

[11] Patent Number: 5,830,224
[45] Date of Patent: Nov. 3, 1998

[54] CATHETER APPARATUS AND METHODOLOGY FOR GENERATING A FISTULA ON-DEMAND BETWEEN CLOSELY ASSOCIATED BLOOD VESSELS AT A PRE-CHOSEN ANATOMIC SITE IN-VIVO

[75] Inventors: William E. Cohn, Chestnut Hill; Ducksoo Kim, Dover, both of Mass.

[73] Assignee: Beth Israel Deaconess Medical Center, Boston, Mass.

[21] Appl. No.: 616,588

[22] Filed: Mar. 15, 1996

[51] Int. Cl.$^6$ ..................................................... A61B 17/32
[52] U.S. Cl. .............................. 606/167; 604/22; 606/167
[58] Field of Search .................................. 606/159, 167, 606/153, 170, 171; 604/22; 128/772

[56] References Cited

U.S. PATENT DOCUMENTS

| | | | |
|---|---|---|---|
| 4,787,884 | 11/1988 | Goldberg | 128/657 |
| 4,874,360 | 10/1989 | Goldberg | 604/8 |
| 5,047,025 | 9/1991 | Taylor et al. | 606/31 |
| 5,087,256 | 2/1992 | Taylor et al. | 606/28 |
| 5,353,807 | 10/1994 | DeMarco | 128/772 |

*Primary Examiner*—Michael Buiz
*Assistant Examiner*—Patrick W. Rasche
*Attorney, Agent, or Firm*—David Prashker

[57] ABSTRACT

The present invention provides catheter apparatus and catheterization methodology for generating an arteriovenous fistula or a veno-venous fistula on-demand between closely associated blood vessels and at a chosen anatomic site in-vivo. The catheter apparatus is preferably employed in pairs, each catheter of the pair being suitable for percutaneous introduction into and extension through a blood vessel. The catheterization methodology employs the catheter apparatus preferably in conjunction with conventional radiological techniques in order to place, verify, and confirm a proper alignment, orientation, and positioning for the catheters in-vivo prior to activating the perforation means for generating a fistula. The invention permits the generation of arteriovenous fistulae and veno-venous fistulae anatomically anywhere in the vascular system of a patient; nevertheless, the invention is most desirably employed in the peripheral vascular system as exists in the extremities of the body to aid in the treatment of the patient under a variety of different medical ailments and pathologies.

2 Claims, 15 Drawing Sheets

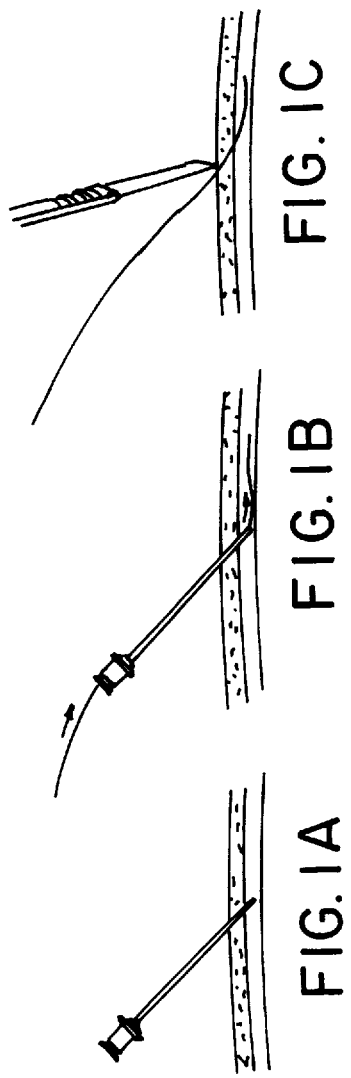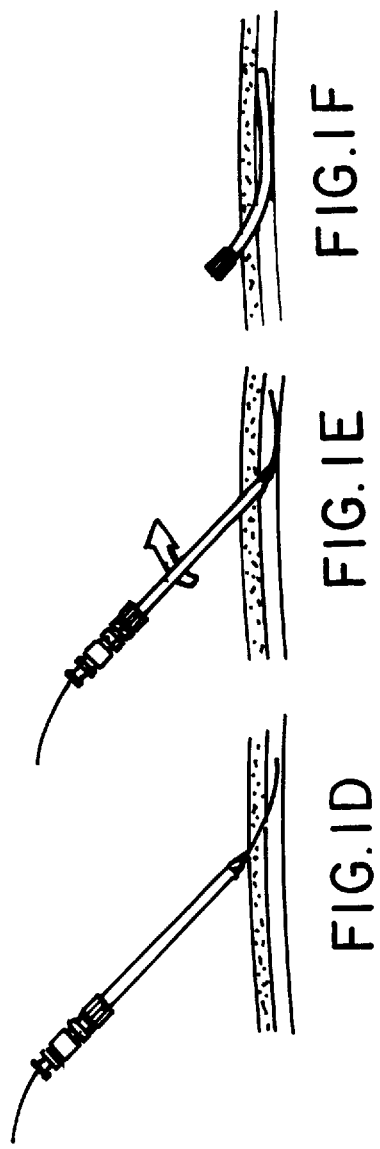

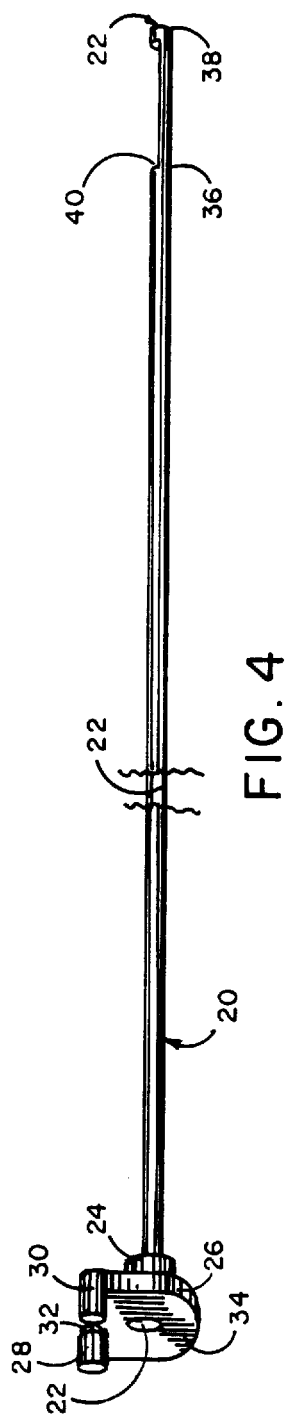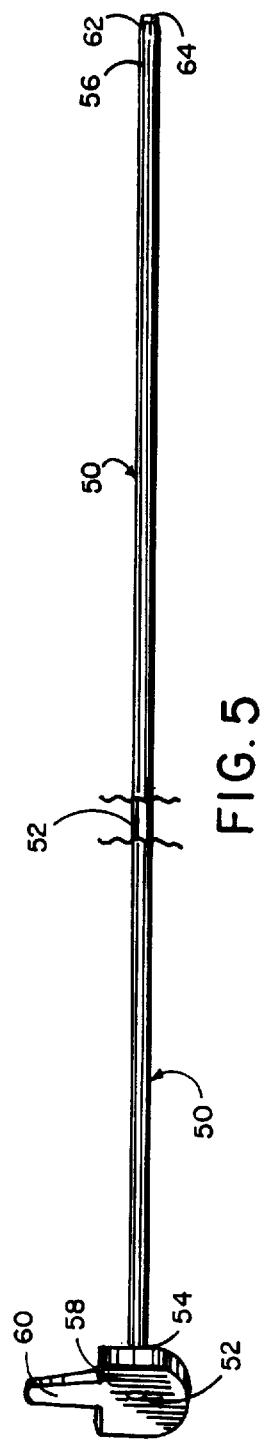

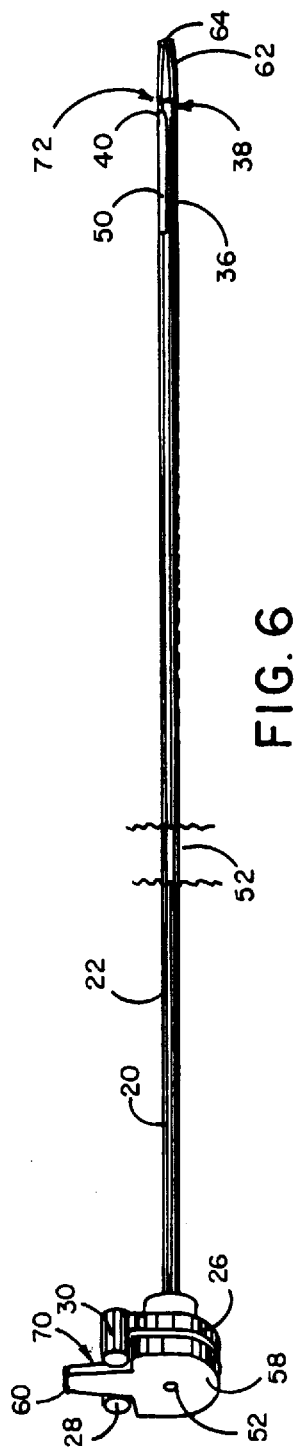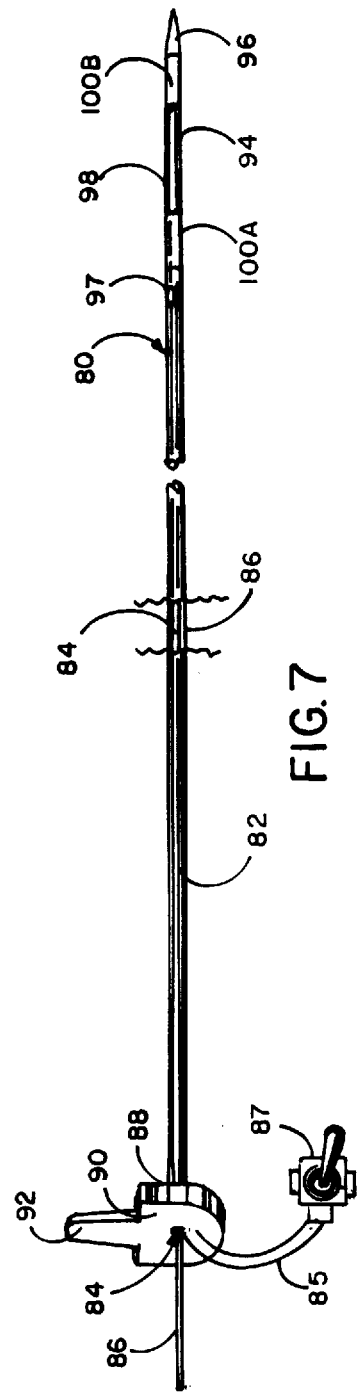

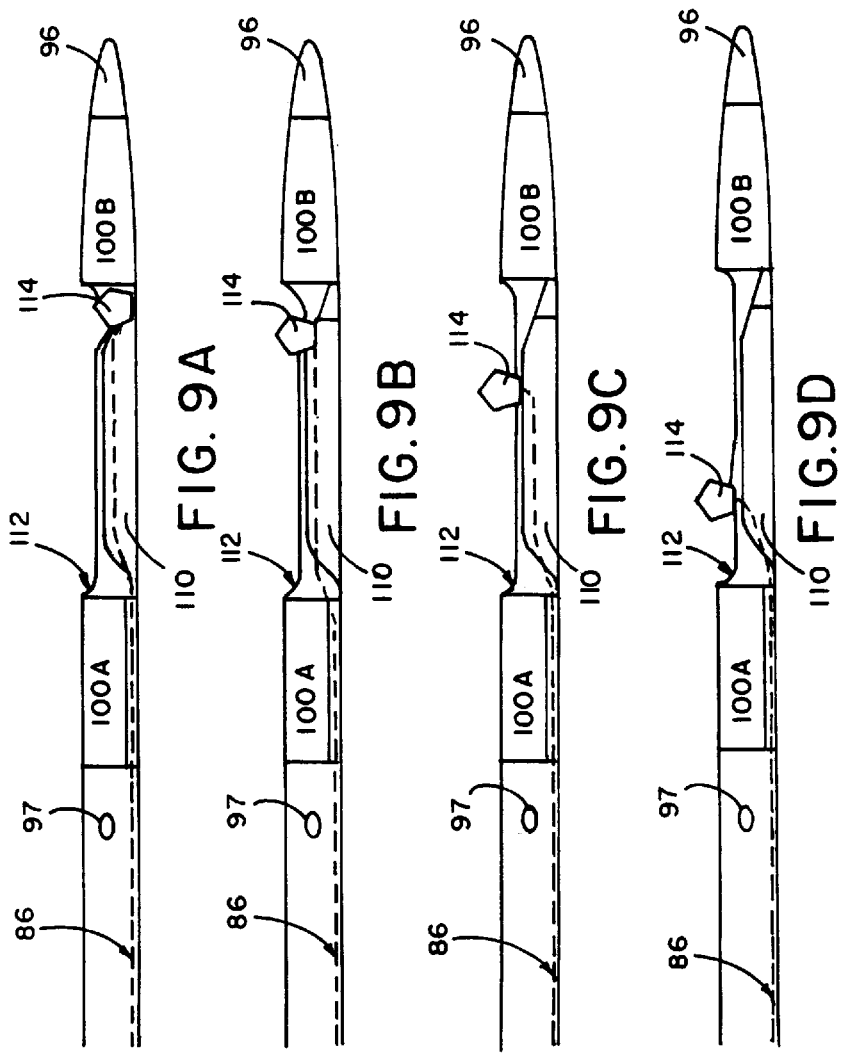

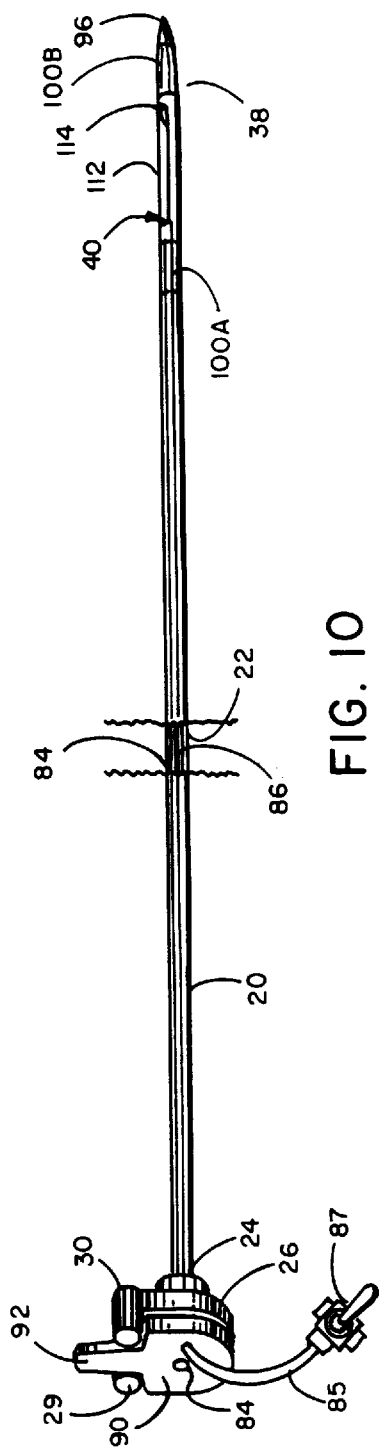
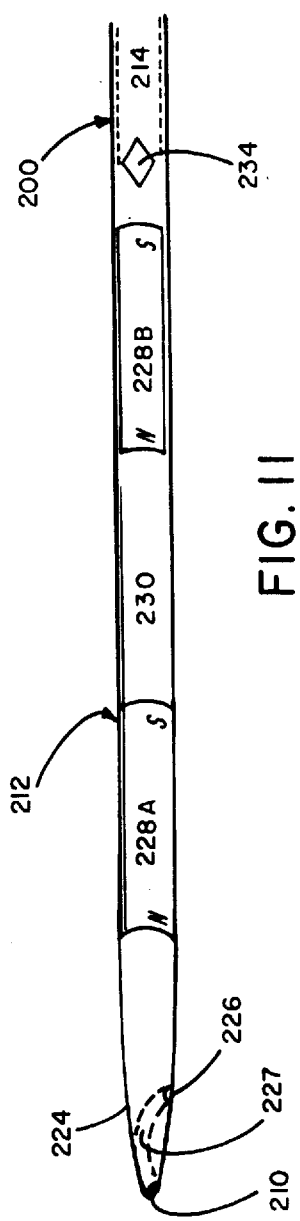

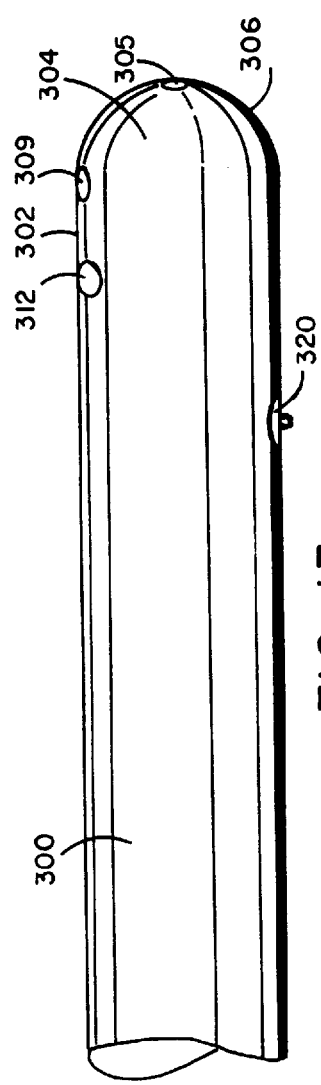
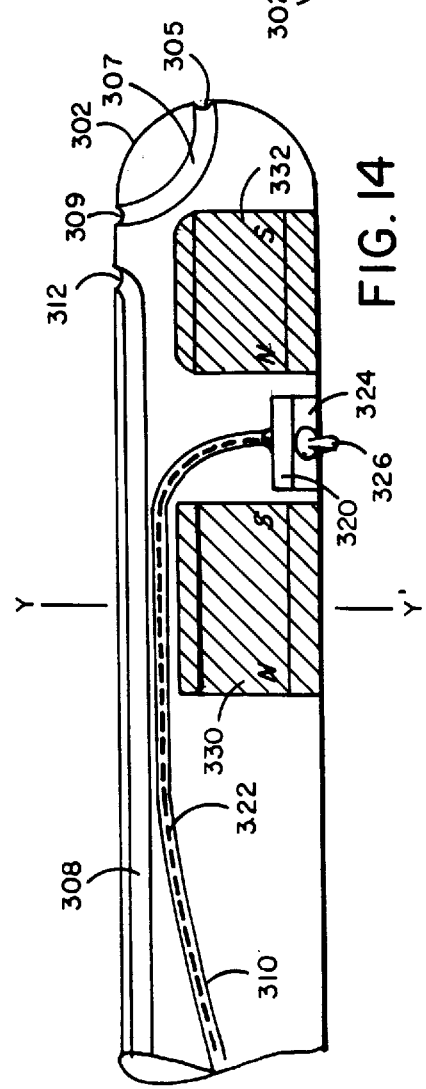
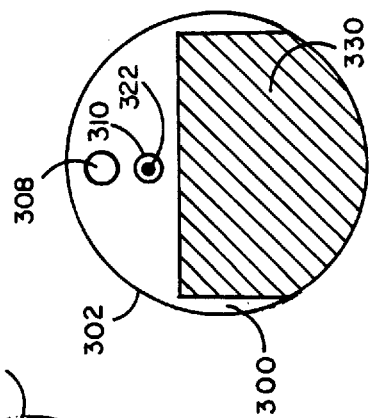

CATHETER APPARATUS AND METHODOLOGY FOR GENERATING A FISTULA ON-DEMAND BETWEEN CLOSELY ASSOCIATED BLOOD VESSELS AT A PRE-CHOSEN ANATOMIC SITE IN-VIVO

FIELD OF THE INVENTION

The present invention is concerned with improvements in catheter design and usage in-vivo; and is particularly directed to catheterization apparatus and methods for creating an arteriovenous fistula or a veno-venous fistula between adjacently positioned blood vessels.

BACKGROUND OF THE INVENTION

A catheter is a long flexible tube introduced into a blood vessel or a hollow organ for the purpose of introducing or removing fluids; implanting medical devices; or for performing diagnostic tests or therapeutic interventions. Catheters are conventionally known and frequently used; and a wide range and variety of catheters are available which are extremely diverse in shape, design and specific features.

Typically a catheter is a long thin tube of fixed axial length, with two discrete, unique ends. One end is designed and engineered to be inserted in the body; the other end generally remains outside the body, and is so designed. Most catheters have at least one internal lumen of a volume sufficient to allow for on-demand passage of a diverse range of wires, rods, liquids, gases, transmitting energy, fiber optics, and specifically designed medical instruments.

The fundamental principles and requirements for constructing a guiding flexible catheter exist as conventional knowledge in the relevant technical field; and all of the essential information is publicly known, widely disseminated, and published in a variety of authoritative texts. The medical and technical literature thus provides an in-depth knowledge and understanding of the diagnostic and therapeutic uses of conventional catheters and commonly used catheterization techniques. Merely representative of the diversity of publications now publicly available are the following, each of which is expressly incorporated by reference here: *Diagnostic And Therapeutic Cardiac Catheterization,* second edition (Pepine, Hill, and Lambert, editors), Williams & Wilkins, 1994 and the references cited therein; A Practical Guide To Cardiac Pacing, fourth edition (Moses et. al., editors), Little, Brown, and Company, 1995 and the references cited therein; *Abrams Angiography,* third edition (H. L. Abrams, editor), Little, Brown & Co., 1983; *Dialysis Therapy,* second edition (Nissenson & Fine, editors), Hanley & Belfus Inc., 1992; and *Handbook of Dialysis,* second edition (Daugirdas & Ing, editors), Little, Brown and Co., 1994.

Thus, in accordance with established principles of conventional catheter construction, the axial length of the catheter may be composed of one single layer or of several layers in combination. In most multilayered constructions, one hollow tube is stretched over another tube to form a bond; and the components of the individual layers determine the overall characteristics for the catheter as a unitary construction. Many multilayered catheters comprise an inner tube of Teflon, over which is another layer of nylon, woven Dacron, or stainless steel braiding. A tube of polyethylene or polyurethane typically is then heated and extruded over the two inner layers to form a firm bond as the third external layer. Other catheter constructions may consist of a polyurethane inner core, covered by a layer of stainless steel braiding, and a third external jacket layer formed of polyurethane.

In addition, a number of dual-lumen catheters are known today which differ primarily in the size and spatial relationship between their individual lumens. Typically, a dual-lumen catheter can take many different forms such as: two co-axially positioned lumens where one small diameter tube extends axially through the internal volume of a larger diameter tube; or the catheter is a single large diameter tube and has a centrally disposed inner septum which divides the interior volume into two equal or unequal internal lumens; or where the material substance of the catheter tube contains two discrete bore holes of differing diameters which serve as two internal lumens of unequal volume lying in parallel over the axial length of the catheter. All of these variations present different dual-lumen constructions for catheters having a similar or identical overall diameter size.

Catheters are generally sized by external and internal diameter and length. The internal diameter is specified either by actual diameter (in thousandths of an inch or millimeters or French size). Many newer thin-walled catheter designs provide a much larger internal lumen volume to external diameter ratio than has been previously achieved; this has resulted in catheters which can accommodate much more volume and allow the passage of much larger sized articles through the internal lumen. External diameter is typically expressed in French sizes which are obtained by multiplying the actual diameter of the catheter in millimeters by a factor of 3.1415 ($\pi$). Conversely, by traditional habit, the actual size of any catheter in millimeters may be calculated by dividing its French size by a factor of $\pi$. As an illustration of size usage. French sizes from 4–8 are currently used for diagnostic angiography. In addition, because of the variation between standard, thin-walled, and super high-flow catheter construction designs, a wide variety of external and internal lumen diameter sizes exist today.

In order to perform effectively in specialized medical procedures and in particular anatomical areas, specific categories or classes of catheters have been developed. Among the presently known specific types of catheters are: peritoneal catheters employed for peritoneal dialysis and which provide dialysate inflow and outflow for the removal of the by-products of metabolism from the blood; acute and chronic urinary catheters introduced into the bladder, the urethra, or directly into the renal pelvis for the removal of urine; central venous catheters are designed for insertion into the internal jugular or subclavian vein; right heart catheters such as the Cournand and Swans-Ganz catheters designed specifically for right heart catheterization; transeptal catheters developed specifically for crossing from right to left atrium through the interatrial septum at the fossa ovalis; angiographic catheters which are used for right or left ventriculography and angiography in any of the major vessels; coronary angiographic catheters which include the different series of grouping including Sones, Judkins, Amplatz, multipurpose, and bypass graft catheters; as well as many others developed for specific purposes and medical conditions.

An illustrative and representative example of traditional catheter usage is provided by the medical specialty of hemodialysis—the process by which extra water and toxic metabolites are removed from the blood by a dialysis machine when the kidneys are impaired by illness or injury. A summary review therefore of renal insufficiency or failure, the technique of hemodialysis, and the role of specialized catheters in machine dialysis will demonstrate and evidence conventional limitations.

A wide variety of pathological processes can affect the kidneys. Some result in rapid but transient cessation of renal function. In patients so affected, temporary artificial filtration of the blood is sometimes necessary. With time, renal function gradually improves and may approach normal; and dialysis is therefore usually required only for a short duration. The time required for the kidneys to recover will depend on the nature and severity of the injury which typically varies from a few days to several months Thus, if the acute condition lasts for more than three or four days, the patient will probably require hemodialysis at least once while awaiting return of renal function.

Other pathological conditions result in a gradual deterioration of renal function over months or years. These patients can go for quite some time before toxic concentrations of metabolites accumulate. Once they reach the stage where dialysis is necessary, however, it is usually required for the rest of their lives. Some of these patients retain low levels of renal filtration and can therefore be dialyzed as infrequently as once a week. Many progress to total renal failure and require hemodialysis two or three times each week. Still other types of renal injury result in rapid onset of permanent renal failure necessitating life long dialysis.

The dialysis machine serves as an artificial kidney to reduce harmful concentrations of the by-products of metabolism and to remove excess water from the blood. The machine is essentially a special filter in series with a blood pump. The filter is connected to the patient via two blood lines. Blood drains from the patient to the dialysis machine through the afferent line; and a volume displacement pump provides suction to assist drainage. The same pump pressurizes the blood to overcome the resistance imposed by the filter. The filter makes use of a semipermeable membrane which separates the blood path from that of dialysate, a special buffered solution used to clear filtered substances. Unwanted molecules diffuse through the semipermiable membrane into the rapidly flowing dialysate and are carried out of the filter in a manner analogous to that of urine flowing through a renal tubule. The membrane is incorporated as multiple pleated sheets or small caliber tubes to increase the surface area across which diffusion may take place. Blood leaving the filter returns to the patient through the second, or efferent, blood line.

The ability to perform dialysis effectively is dependent on high flow of blood through the filter. Furthermore, blood must be returned to the patient as rapidly as it is withdrawn to prevent the hemodynamic consequences of large fluctuations in intravascular volume. It is therefore necessary that both afferent and efferent blood conduits be connected to the patient by way of transcutaneous catheters inserted into large bore, high flow blood vessels.

For patients in whom renal recovery is anticipated, percutaneous intravenous access is used frequently. This technique makes use of a large bore flexible two-lumen catheter. This catheter, measuring 10 French, (roughly 3 mm in diameter) is introduced into the central venous circulation via the subclavian or internal jugular vein. Placement of transcutaneous venipuncture in conjunction with the Seldinger technique and serial dilation is used; and the tip of the catheter is positioned at the junction of the superior vena cava and the right atrium. Alternatively, the catheter is placed percutaneously in the femoral vein. Blood is withdrawn from one lumen and returned through the other. The afferent lumen ends 2 or 3 centimeters from the catheter tip which inhibits recirculation of efferent blood. The large size and high blood flow of the superior vena cava permits very effective dialysis with this technique.

Unfortunately, however, this method of percutaneous intravenous access is not well suited for patients who will require long term or permanent dialysis. The presence of a foreign body (the access catheter) breaching the skin is associated with a high risk of infection. This risk increases with time, and in long term applications, is prohibitive. Because the foreign body is in an intravascular location, the infection is usually associated with sepsis, or infection of the blood stream, which can be lethal. Special catheters are designed to be implanted or "tunneled" subcutaneously for several centimeters to decrease the incidence of sepsis; and if absolutely sterile technique is used when manipulating the catheter (and the skin exit site is meticulously cleaned and dressed), these tunneled catheters can be used for several months without incident. Despite pristine care, however, infection is inevitable with extended use; and all such catheters eventually must be removed. Aside from sepsis, long term central venous access is also associated with a time related increase in the risk of endocarditis, cardiac perforation from catheter tip erosion, and superior vena cava thrombosis. Patients who require permanent or lifetime hemodialysis therefore must be attached to the dialysis machine in a different way.

Two methods have evolved to provide long term vascular access in patients on permanent dialysis. The first method involves surgically implanting a 6 or 8 mm dacron or gortex tube graft subcutaneously in the upper extremity. A small transverse incision is made in the proximal forearm, just below the crease. One end of the tube graft is anastomosed to the side of the brachial artery and the other, to the side of a large antecubital vein. The body of the graft between the two anastomoses is tunneled just below the skin in a horseshoe configuration, with the bend at the mid forearm. Blood flowing through the tube bypasses the capillary bed, and as such, represents a very low resistance pathway. This surgically created "short circuit" in the circulatory system is referred to as a shunt. The low resistance in the shunt results in a high blood flow. To perform hemodialysis, two large bore needles are sterilely introduced into the graft lumen through the intact skin. This can be readily accomplished as the graft, in its subcutaneous location, is easily palpated. The large lumen and high blood flow provide excellent drainage for dialysis. After hemodialysis is completed, the needles are removed, so no permanent breech in the skin exists. Each time the patient is dialyzed, needles are reintroduced.

The second method involves the creation of a direct arteriovenous fistula between the radial artery and an adjacent vein—without the use of a prosthetic graft material. Once again, the capillary network is bypassed, and a low resistance "short circuit" in the circulatory system results. The direct and increased volume of blood flow through the fistula leads to massive venous dilation. Dialysis catheters are then introduced into the dilated veins.

To create an arteriovenous fistula for permanent hemodialysis, an incision is made at the wrist and the radial artery identified and mobilized. An adjacent vein is mobilized as well. After obtaining vascular isolation with vessel loops or soft clamps, the artery and vein are opened longitudinally for a distance of 5 to 8 mm. Using fine monofilament suture and magnified visualization, the arteriotomy and venotomy are sewn together, creating a side-to-side anastomosis (or, alternatively, the end of the vein is sewn to the side of the artery). This surgically created connection allows blood to bypass the capillary bed, and results in dramatically increased flow through the forearm veins. In contrast to the shunt technique of the first method, there is no easily palpable prosthetic graft just beneath the skin that can be entered transcutaneously. However, because the arteriovenous fistula is performed at the wrist, the thin-walled forearm veins are subjected to high blood flow; and, over a short period of time, dilate to 2–3 times their initial size. The massively dilated veins are easily identified and can be accessed by two large bore needles as described above for the shunt.

Each of the two surgical techniques has relative advantages and disadvantages. The shunt, although simple to construct, involves implantation of a foreign body. Each time a needle is introduced percutaneously, there is risk of infection of the graft with skin organisms. The risk of infection is not as great as was described for the indwelling intravenous dialysis catheters, but is still present. With meticulous attention to sterile technique, shunts of this type can be maintained for years. Hemodialysis patients often have impaired immune systems, however, and infection requiring shunt removal is not uncommon. A second problem seen with prosthetic shunts is that of thrombosis necessitating thrombectomy or revision. Reactions take place between the prosthetic material and the platelets in the blood that result in liberation of clotting factors. These factors stimulate abnormal growth of the intima, or lining of the vein, at the venous anastomosis. This abnormal growth narrows the anastomosis resulting in decreased flow through the graft and thrombosis. Hemodialysis patients often require multiple operations for thrombectomy and shunt revision throughout their lives to maintain vascular access.

The direct arteriovenous fistula method is highly desirable and advantageous in that no prosthetic material is implanted; and the risk of infection is therefore dramatically reduced. In addition, all blood carrying surface are lined with living intima, and intimal proliferation is very uncommon. Moreover, the vein, being composed of living tissue, has the ability to mend itself and is less likely to form pseudoaneurysms as is occasionally seen with prosthetic shunts after extended use. For these reasons, most surgeons prefer to perform this procedure when it is technically feasible.

Unfortunately, in many patients, use of an arteriovenous fistula is technically not possible by conventional means. As described above, the radial artery is dissected out at the wrist; and a distal dissection zone is preferred in that more veins will be subjected to increased flow and dilation, resulting in more potential sites for hemodialysis needle insertion. However, the radial artery is somewhat small at this distal location which makes anastomosis technically more demanding, especially in smaller patients. Furthermore, because a direct anastomosis must be constructed, a relatively large vein is needed in the immediate vicinity of the radial artery, and this is not always present. In the alternative, if a vein more than a centimeter away is mobilized and brought over to the artery, venous kinking can occur which results in decreased flow and early thrombosis. In addition, mobilization of the vein disrupts the tenuous vasovasorum, the miniscule arteries that provide blood supply to the vein wall itself, which can result in fibrosis of the vein wall and constriction of the vein lumen. This sets the conditions for early fistula failure.

Note also that each of the procedures described above must be done in the operating room. Most of the patients thus receive intravenous sedation and must be monitored postoperatively in a recovery room environment. Some remain hospitalized for a day or more as per the surgeon's preference. It is well known that individuals with renal failure exhibit impaired wound healing and a compromised immune function. These patients are therefore at increased risk for developing postoperative wound complications.

The conventional and limited usage of specialized catheters as examplified by the medical practice of hemodialysis is thus well demonstrated and revealed. Clearly, despite the recognized desirability and advantage of creating an arteriovenous fistula for long-term or life-use patients needing dialysis, the use of catheters has remained limited and used primarily for the introduction and removal of fluids while the creation of arteriovenous fistulae remains the result of skilled surgical effort alone. Thus, although there is a long standing and well recognized need for an improved procedure and/or vehicle for generating arteriovenous fistulae, no meaningful alternative has been developed to date; and no catheter-based methodology or protocol has ever been envisioned as suitable for on-demand generation of an arteriovenous fistula in-vivo.

SUMMARY OF THE INVENTION

The present invention has multiple aspects and formats. One aspect of the invention provides a catheter for generating an arteriovenous fistula or a veno-venous fistula on-demand between closely associated blood vessels at a chosen anatomic site in-vivo, said catheter being suitable for percutaneous introduction into and extension through a blood vessel and comprising:

(a) a tube having a fixed axial length, a discrete proximal end, a discrete distal end, and at least one internal lumen of predetermined volume;

(b) a distal end tip adapted for intravascular guidance of said tube through a blood vessel in-vivo to a chosen anatomic site;

(c) magnet means positioned at said discrete distal end and set in axial alignment with said distal end tip of said tube, said magnet means having sufficient magnetic force to cause an adjustment in position for said tube when in proximity with a source of magnetic attraction disposed within a closely associated blood vessel;

(d) vascular wall perforation means positioned at said discrete distal end adjacent to said magnet means and set in axial alignment with said distal end of said catheter, said magnet means having sufficient magnetic strength to cause an adjustment in position for said catheter when in proximity with an alternative source of magnetic attraction disposed within a closely associated blood vessel;

(d) vascular wall perforation means positioned at said discrete distal end adjacent to said magnet means and set in axial alignment with said distal end tip of said tube, said vascular wall perforation means becoming intravascularly adjusted in position via the magnetic force of said magnet means when in proximity with a source of magnetic attraction disposed within a closely associated blood vessel in-vivo; and (e) means for activating said vascular wall perforation means of said tube on-demand wherein said vascular wall perforation means perforates the chosen anatomic site to generate a fistula in-vivo between the closely associated blood vessels.

A second aspect of the present invention provides a catheterization method for generating an arteriovenous fistula or a veno-venous fistula on-demand between closely associated blood vessels at a chosen anatomic site in-vivo, said catheterization method comprising the steps of:

procuring at least one catheter suitable for percutaneous introduction into and extension through a blood vessel in-vivo to a chosen anatomic site, said catheter being comprised of (a) a tube having a fixed axial length, a discrete proximal end, a discrete distal end, and at least one internal lumen of predetermined volume, (b) a distal end tip adapted for intravascular guidance of said tube through a blood vessel in-vivo to a chosen anatomic site, (c) magnet means positioned at said discrete distal end and set in axial alignment with said distal end tip of said tube, said magnet means having sufficient magnetic force to cause an intravascular adjustment in position for said catheter when in proximity with a source of magnetic attraction disposed within a closely associated blood vessel in-vivo.

(d) vascular wall perforation means positioned at said discrete distal end adjacent to said magnet means and set in axial alignment with said distal end tip of said tube, said vascular wall perforation means becoming intravascularly adjusted in position via the magnetic force of said magnet means when in proximity with a source of magnetic attraction disposed within a closely associated blood vessel in-vivo, (e) means for activating said vascular wall perforation means of said catheter on-demand wherein said vascular wall perforation means perforates a chosen anatomic site in-vivo between closely associated blood vessels;

percutaneously introducing said catheter into a first blood vessel and extending said catheter intravascularly to a chosen anatomic site adjacent to a closely associated blood vessel;

percutaneously introducing a source of magnetic attraction into a closely associated second blood vessel and extending said source of magnetic attraction intravascularly to the chosen anatomic site to be in transvascular proximity to said extended catheter;

permitting a transvascular magnetic attraction to occur between said magnetic means of said extended catheter in the first blood vessel and said source of magnetic attraction in the closely associated second blood vessel whereby said vascular wall perforation means of said catheter comes into transvascular alignment with the closely associated second blood vessel; and then activating said vascular wall perforation means of said catheter on-demand wherein said vascular wall perforation means perforate the vascular walls of said closely associated blood vessels concurrently at the chosen anatomic site to generate a fistula in-vivo.

BRIEF DESCRIPTION OF THE FIGURES

The present invention may be more completely and easily understood when taken in conjunction with the accompanying drawing, in which:

FIGS. 1A–1E illustrate of the modified Seldinger technique as a series of manipulative steps;

FIG. 4 is an overhead view of the venous introducer cylinder forming a component part of the preferred venous catheter of FIG. 2;

FIG. 5 is an overhead view of the venous obturator fitting into the introducer cylinder of FIG. 4 and forming a component part of the preferred venous catheter of FIG. 2;

FIG. 6 is an overhead view of the venous introducer cylinder of FIG. 4 and the venous obturator of FIG. 5 in combination;

FIG. 7 is an overhead view of the tubular cutting tool forming a component part of the preferred venous catheter of FIG. 2;

FIGS. 9A–9D are sequential sectional views demonstrating the consequence of activating the vascular well perforation means in the tubular cutting tool of FIG. 7;

FIG. 10 is an overhead view showing the venous introducer cylinder of FIG. 4 and the tubular cutting tool of FIG. 7 in combination;

FIG. 11 is a side view of the distal end of the arterial catheter of FIG. 3;

FIG. 13 is a side view of the distal end of a second alternative embodiment of a catheter suitable for generating an arteriovenous fistula in-vivo;

FIG. 14 is an axial-section view of the alternative catheter embodiment of FIG. 13;

FIG. 15 is a cross-section view of the second alternative catheter embodiment of FIG. 13 along the axis YY';

DETAILED DESCRIPTION OF THE PRESENT INVENTION

Figure 2:
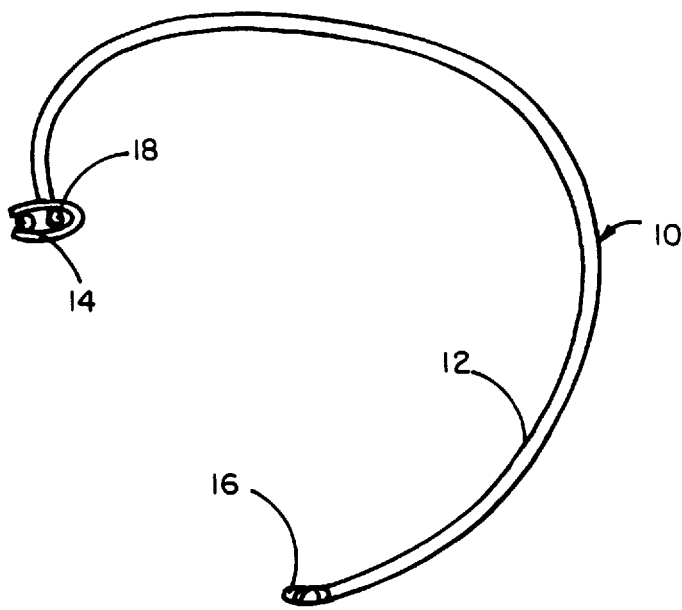
FIG. 2 is an overhead view showing a preferred embodiment of a venous catheter used to generate an arteriovenous fistula.

The present invention is a percutaneous arteriovenous fistula catheter (hereinafter "PAVFC") apparatus and methodology which will generate a fistula between an adjacently located artery and vein or an adjacently located pair of veins in the peripheral vascular system. The arteriovenous (hereinafter "AV") fistula or veno-venous fistula (hereinafter "VV") is created in a controlled manner between closely associated blood vessels, ideally in the distal extremities (arms or legs) of the patient. However, usage at any anatomic site is possible; and the AV (or VV) fistula can be generated on-demand at a prechosen vascular site under carefully monitored clinical conditions. As such, the present invention provides multiple advantages and unique benefits to both the physician and the patient, some of which include the following.

1. The present invention is not a surgical procedure as such. To the contrary, the PAVFC apparatus and methodology is a radiological technique which avoids the use of surgical incisions and procedures and eliminates the need for surgically created AV (and VV) fistulas. It is well recognized that chronically ill patients such as renal failure patients have an impaired wound healing capacity; are subject to an increased incidence of infection after surgery; and are subject to a high risk of hemorrhage as a consequence of surgical procedures. The present invention permits the generation of AV (or VV) fistulas without necessitating surgery or surgical incision, thereby reducing the risk to the chronically ill patient. In addition, by the avoidance of surgical procedures as such, the need for an operating room, an anesthesiologist, and surgical nursing staff is obviated.

2. The present invention allows for AV or W fistula formation in anatomical areas where surgical procedures would be difficult, if not impossible, to perform. For example, in hemodialysis, surgical access for the creation of an AV fistula is often limited to the distal radial artery. However, often there is not an adjacently positioned or closely associated distal vein of sufficient size in the same anatomical area which is surgically accessible. In comparison, the PAVFC technique comprising the present invention generates fistula in the peripheral vascular system between closely associated arteries and veins where traditional surgical exposure would be impossible in most instances. Accordingly, the present invention allows for and has the potential to utilize many more vascular sites in the peripheral circulation as locations for the generation of an AV fistula on-demand.

3. The present invention allows for the identification and evaluation of juxtapositioned blood vessels in the entire extremity (preferably by use of intravascular ultrasound to identify the most favorable anatomical site) in order to provide an accurate assessment of venous diameter at a specific vascular site prior to performing the technique to generate an AV or VV fistula. Peripheral veins of small diameter or having thin walls which are typically unsuitable for surgical anastomosis are easily located and now become available for use; and the determination of whether or not a portion of the venous vascular wall is closely associated with and lies adjacent to an artery (or vein) can be routinely made.

4. The present apparatus and methodology allows the radiologist to determine with substantial certainty whether or not a suitable vein exists in the vicinity of a closely associated peripheral artery (or vein) prior to beginning the requisite sequence of steps necessary to generate a fistula. Not only is the juxtapositional determination made, but also the specific site is chosen in advance which provides the best combination of anatomical circumstances (including anatomic location, arterial venous proximity, arterial diameter, and venous diameter). In this manner, the radiologist may thoroughly consider a given vascular site for generating the fistula; determine whether or not to seek a more favorable location in the same closely associated vein and artery or in another artery and vein in the same extremity; or whether to redirect the catheter apparatus into another extremity in order to find a more favorable anatomical site.

5. The apparatus and method of the present invention also provide a most important benefit in that the blood vessels are not dissected out or manipulated as a prerequisite of AV fistula formation. The tenuous vaso vasorum therefore remains preserved in the naturally occurring state, a circumstance which improves vascular patency. This benefit stands in contrast to the loss of the vaso vasorum and other undesirable consequences of vascular manipulation necessitated by conventional surgical AV or VV fistula creation which cause injury to the delicate vein wall and result in contraction of the vein—a condition which limits the vein's ability to dilate and may contribute to early fistula failure. Moreover, although introducing the catheter of the present invention into a vein may be traumatic to the venous endothelium at the site of entry, the injured segment of the vein will be distal to the AV fistula, and patency of this injured segment is not necessary for proper fistula function. In addition, as the procedure for fistula formation is performed at sites of close arterial venous approximation, no venous distortion or kinking occurs or is necessary in the creation of the fistula.

6. The present invention provides far less risk to the critically or chronically ill patient in comparison to conventional surgical procedures for creation of AV (or VV) fistulae. The PAVFC technique offers fewer potential problems than routinely occur with conventional surgical procedures; and these relatively few potential problems relate primarily to the risk of hemorrhage. However, even this potential risk of hemorrhage is deemed to be small; is clinically obvious if and when it occurs; and is readily controlled with direct pressure using a conventional blood pressure cuff or manual compression.

7. The present invention is intended to be employed in multiple use circumstances and medical applications. An envisioned and particularly desirable circumstance of usage is to provide long term vascular access for hemodialysis for those patients requiring permanent or long term dialysis. Additionally, the PAVFC technique can be used to create AV fistulae for the administration of caustic chemotherapeutic agents. In each of these instances, the PAVFC technique will not only identify one or more favorable vascular sites in the radial and ulnar arteries along their peripheral length, but also will identify other adjacently positioned veins and the most desirable anatomical sites within the closely associated vein, particularly when lying within the distal portion of the forearm. In addition to these particular usages, the present invention allows for the generation of an AV or VV fistula for any other medical purpose, condition, or circumstance. Thus, the PAVFC technique can also be desirably used for creation of additional vascular interconnections in the peripheral blood circulation between arteries and veins; to generate a greatly enlarged blood vessel segment in the peripheral vascular system which then would be surgically excised and employed as a vascular bypass graft or harvested on a pedicle in another anatomical area; and to generate on-demand alternative blood circulation pathways between arteries and veins in the peripheral vascular system when blockages and other vascular obstructions exist.

In order to facilitate ease of understanding and to provide a complete and comprehensive description of the present invention in all its aspects, a detailed disclosure of the catheter apparatus and methodology will be presented in separate sections seriatim. The presentation will be made in the following sequence: A description of the theoretical support for the technique; a summary of conventional procedures for surgically introducing and routing a catheter into the body of a living human; a description of the preferred and several alternative catheter embodiments comprising the present invention; an illustrative example showing the intended usage of the catheter apparatus in-vivo; and a representative description of some intended applications and use circumstances for the present invention. Taken cumulatively and collectively, the entirety of the disclosure not only describes embodiments of the preferred and alternative catheter apparatus but also enables the reader to make and use the present invention productively without major difficulty or doubt.

I. Theoretical Support for the Invention

The present invention intends and expects the radiologist or attending physician to create a fistula in-vivo between an adjacently positioned and closely associated vein and artery (or between two closely associated veins) in the peripheral vascular system of a chronic or critically ill patient. In effect and result, therefore, the present invention generates a direct flow connection between a functioning artery and vein (or between two functioning veins) without the existence or usage of intervening capillaries.

To generate the AV fistula, the present invention perforates the immediately adjacent vascular walls of both the vein and the artery concurrently, directly, and in tandem. Moreover, unlike conventional surgical procedures to create fistulas and shunts, there are no sutures used to join the vascular walls at the point of perforation; and no synthetic or artificially introduced means for joining or attaching the perforated vein to the perforated artery are employed in order to obtain hemostasis at the point of anastomosis. It may therefore seem counterintuitive to the reader that an AV fistula can be generated as described without exsanguination into the arm or leg of the patient and without risk of blood loss or even death as a consequence of performing the methodology.

The principle that enables an arteriovenous fistula to be created in this way, however, is clearly demonstrated clinically and is encountered frequently. Unintended acquired arteriovenous fistulas are encountered occasionally in evaluation of patients with penetrating trauma such as knife stabbings, gun-shot holes, and other perforations of the body caused by violent acts. Physical exam of the wound in these individuals demonstrates venous engorgement of the involved extremity in conjunction with an audible bruit or even a palpable venous thrill. Subsequent arteriogram of the wound area demonstrates an arteriovenous fistula in the vicinity of the knife or missile tract. Other patients also with vascular injury after penetrating trauma, however, do not develop arteriovenous fistulae. Most of these patients are found instead to have a pulsatile mass without pronounced venous engorgement; and an arteriogram of these patients demonstrates a pseudoaneurysm or contained rupture of the injured vessel. Note that these two types of injuries are almost never seen in tandem. It is extremely unusual for a patient with an arteriovenous connection to have a pseudoaneurysm, and vice-versa. Similarly, some patients develop an arteriovenous connection between the common femoral artery and the femoral or saphenous vein as a complication of percutaneous arterial access, whereas others develop pseudoaneurysms; but the two clinical findings are almost never seen together in one patient. Yet all of these patients are similar in that they have sustained substantial injury to a sizable artery. The difference in clinical findings thus lies in the spatial relationship existing between the injured blood vessels in-vivo.

In each example cited above, the patient has sustained an arterial vascular injury, either by knife, bullet, or angiographic needle. The tissues surrounding the peripheral artery are adherent to the adventia (or outer layer of the artery wall), but can be dissected off by an expanding hematoma. The blood extravasating through the arterial injury does so at arterial pressure which provides the force necessary for the continued expansion. The hematoma (or clotted blood collection) lyses within a day or two, leaving a juxta-arterial cavity that communicates with the vessel lumen. The resulting clinical finding is that of pseudoaneurysm. In some patients, however, there is also a closely associated venous injury concurrent with the arterial damage. If the venous injury is of sufficient size and appropriate orientation, an arteriovenous fistula results. Blood leaves the artery through the arterial injury; flows along the knife or missile tract; and enters into the vein through the venous injury. Moreover, because the venous system has such low resistance, the hydrodynamic pressure generated in the vicinity of the injury is not sufficient to cause a dissecting hematoma. The high flow velocity between the artery and vein maintains the patency of the fistula thereafter.

It can be properly believed that every penetrating injury to an extremity is associated with multiple arterial and venous injuries of various sizes. The likelihood of developing an arteriovenous fistula after penetrating injury is thus related to the caliber of the blood vessels injured and the vascular geometry of the injury. If clean, linear perforations are made in immediately adjacent walls of 3–4 mm blood vessels, a fistula would almost certainly develop; and extravasation and pseudoaneurysm formation would be most improbable and highly unlikely.

The present invention thus relies on this clinical basis for support; provides a catheter apparatus and a methodology by which to access adjacently located arteries and veins in the extremities; and presents the means by which to generate a perforation on-demand at a chosen anatomic site in the peripheral vascular system between a closely associated artery and vein such that an aperture or hole is bored or otherwise created concurrently through both the adjacent arterial and venous walls. A direct blood flow connection is thus generated by which arterial blood passes through the perforation in the arterial wall and into the vein lumen, through the aligned perforation in the immediately adjacent, low resistance vein. The underlying principle and basis is clinically established and documented; and there is no meaningful doubt or uncertainty that an AV fistula can be created on demand and in-vivo within the extremities of the patient in a safe and reliable manner using the apparatus of the present invention, standard catheterization techniques, and conventionally known radiological procedures.

II. Surgical Introduction And Routing Of A Catheter Into The Body Of The Living Human Catheterization involves a great deal of technical skill, complex instrumentation and mature judgment in order to choose among the appropriate procedures and the various techniques which are now conventionally known and commonly available. Clearly, because the present PAVFC technique utilizes catheter intervention in critically or chronically ill patients, the physician must be very familiar with the available anatomical alternatives for accessing the peripheral vascular system in order to select the best site for introducing the catheter, the best route to the desired area of the body, and the optimal timing and other operative conditions in order to achieve the best results.

Catheterization as a general technique can be performed using any duct, tube, channel, or passageway occurring naturally or surgically created for the specific purpose. Thus, among the naturally occurring passageways are the anus; the alimentary canal; the mouth, ear, nose, or throat; a bronchus; the urethra; the vaginal canal and/or cervix; and any blood vessel. However, clearly the most common used and critical route of access for the present invention is the introduction of catheters into the vascular system. For this reason, it is useful to describe conventional guiding catheters, and to briefly summarize the technique currently in use for introduction of catheters into the vascular system as an illustrative example of general catheterization techniques.

Catheter Introduction Techniques

There are two general methods currently in use for catheterization. These are: (a) percutaneous introduction using needles and guidewires; and (b) direct introduction after surgical isolation of the blood vessel of choice. While either general method may be utilized at any site of the vascular system, practical and anatomical considerations will generally dictate which approach is most appropriate under the individual circumstances. Most often, however, the modified Seldinger technique is favored for use.

The percutaneous introduction of a catheter is best illustrated by the modified Seldinger technique which is conventionally known and shown by FIGS. 1A–1F. FIG. 1A shows a blood vessel being punctured with a small gauge needle. Once vigorous blood return occurs, a flexible guidewire is placed into the blood vessel via the needle as shown by FIG. 1B. The needle is then removed from the blood vessel, the guidewire is left in place, and the hole in the skin around the guidewire is enlarged with a scalpel as shown by FIG. 1C. Subsequently, a sheath and a dilator is placed over the guidewire as shown by FIG. 1D. Thereafter, the sheath and dilator is advanced over the guidewire directly into the blood vessel as shown by FIG. 1E. Finally, the dilator and guidewire is removed while the sheath remains in the blood vessel as illustrated by FIG. 1F. The catheter is then inserted through the sheath and fed through the blood vessel to reach the desired location.

The other general method for the introduction of catheters into the blood circulation is direct surgical cutdown. The surgical cutdown approach is generally used for the brachial approach or the femoral approach. Cutdown procedure is often a complex surgical procedure and is used only when percutaneous arterial puncture (as described above) has been unsuccessfully attempted. A far more complex and fully descriptive review of both these general catheterization techniques is provided by the texts of: *Diagnostic And Therapeutic Cardiac Catheterization,* second edition, 1994, Chapter eight, pages 90–110 and the references cited therein.

Accordingly, for purposes of practicing the present methodology, any and all generally known catheterization procedures, apparatus, and techniques which are conventionally employed and are in accordance with good medical practice are explicitly intended to be utilized as necessary in their original format or in a modified form. All of these general catheterization routing and use techniques are thus envisioned and are deemed to be within the scope of the present invention.

General Rules For Choosing An Appropriate Site of Body Entry:

An axiomatic or general set of rules by which a physician can choose a proper or appropriate site of entry for introducing a guiding catheter into the vascular system of a patient for purposes of performing diagnostic tests or therapeutic interventions in-vivo is as follows: (a) always pick the shortest and straightest pathway possible or available; (b) identify the patency of an existing and accessible artery or vein, the larger the diameter of the blood vessel the better; and (c) avoid arteries with obvious calcification or atheromatous involvement.

A favored Approach to Introducing the Catheter Into the Body:

(1) The intended site for entry is prepared and draped in a sterile fashion.

(2) The skin over the large bore artery or vein is infiltrated with 1% lidocaine for local anesthesia.

(3) A small skin nick is made over the anesthetized area.

(4) Via the skin nick, the large bore artery or vein is punctured using a single wall puncture needle.

(5) The amount and nature of blood returning through the needle is evaluated for proper needle position.

(6) A 0.035 inch or 0.038 inch guide wire is passed via the needle into the blood vessel.

(7) A 4–9 French dilator is passed coaxially over the wire and then is removed.

(8) A hemostatic 4–9 French introducer sheath and obturator are passed coaxially over the wire; and the obturator and wire are then removed.

(9) Via the hemostatic introducer sheath, the guiding catheter is passed through the blood vessel and located at the intended use site.

The description provided herein is merely a summary review of the means and manner by which a catheter is properly introduced into the body of a living human patient. The physician is presumed to be well acquainted and sufficiently experienced in all these general catheterization techniques; and the choices of which manner or mode or usage is preferable to another must be left to the medical discretion and judgment of the physician given the specific problems and ailments of his patient.

III. The Unique Catheter Apparatus

The catheter apparatus comprising the present invention can take many different and alternative forms and be constructed in a diverse range of widely different embodiments. As a favored approach, it is generally desirable that the catheter apparatus comprise two discrete catheters introduced into the body independently but employed in tandem in order to generate an AV fistula in-vivo. Nevertheless, in certain limited medical instances and under demanding medical circumstances, it is both envisioned and acceptable to employ a single catheter alone for percutaneous introduction and extension through a vein or artery in order to generate an AV fistula on-demand. Thus, although the use of a single catheter independently is the least desirable format and mode of usage of the present invention, the single catheter construction and usage nevertheless will serve and provide the means for generating an AV fistula between an adjacently positioned artery and vein at a chosen anatomic site in-vivo. However, if the physician has a choice given the particular circumstances and ailments of his patient, it is far more desirable that a pair of catheters be employed concurrently and in tandem in order to achieve a far greater degree of certainty and reliability in the outcome.

A. A Preferred First Embodiment

A highly preferred embodiment of the catheter apparatus able to generate an AV fistula on-demand between a closely associated artery and vein at a chosen anatomic site in-vivo employs a pair of uniquely constructed catheters concurrently and in-tandem. The first catheter of the pair is suitable for percutaneous introduction and extension through a vein in-vivo to a chosen intravenous location and is illustrated by FIG. 2. As exemplified by FIG. 2, a venous catheter 10 is seen having a hollow tubular wall 12 of fixed axial length; an interlocking proximal end 14 for the catheter 10; a discrete distal end 16 and a co-axial internal lumen 18 which extends from the interlocking proximal end 14 to the distal end 16. Other features of the venous catheter 10 are described hereinafter.

Figure 3:
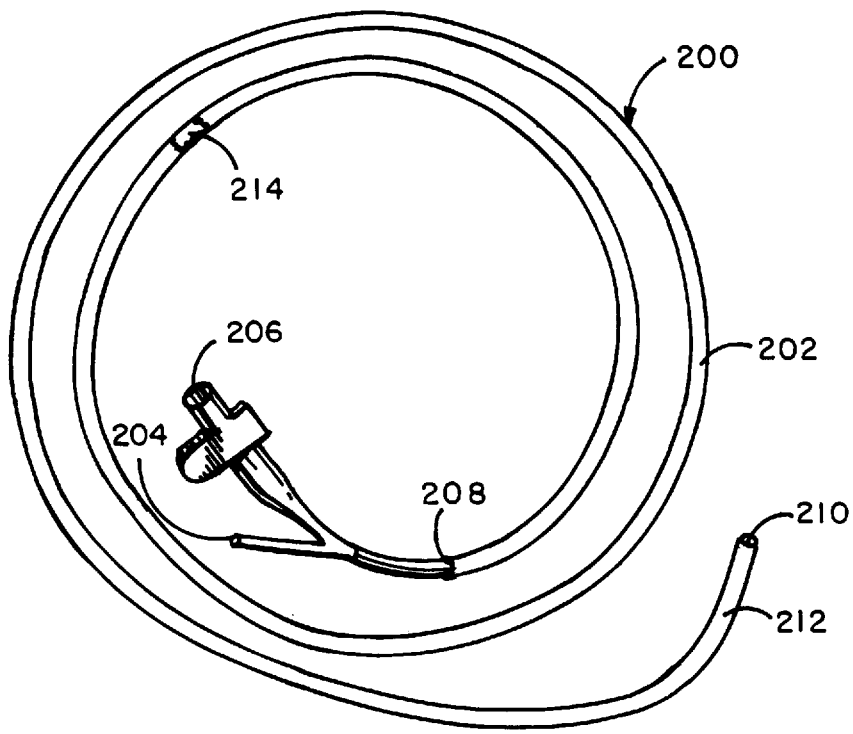
FIG. 3 is an overhead view showing a preferred embodiment of an arterial catheter used to generate an arteriovenous fistula.

The second of the pair in this preferred embodiment of the catheter apparatus is exemplified by FIG. 3 which illustrates a second catheter suitable for percutaneous introduction into and extension through an artery in-vivo to a chosen intraarterial site. As exemplified by FIG. 3, an arterial catheter 200 is seen having a hollow tubular wall 202 of fixed axial length; two proximal portals 204, 206 which together form a discrete proximal end 208 for entry into the internal volume of the catheter 200; a single discrete distal portal 210 for passage of a guidewire; and a discrete distal end 212; and an internal lumen 214. Additional details for the arterial catheter are described hereinafter.

In this preferred embodiment, the construction, some specific features, and the designated purpose for each catheter in the pair are markedly different. While each catheter in the pair share common features for purposes of location finding and placement intravascularly, this preferred embodiment of the apparatus employs the venous catheter as the active source and physical means by which the vascular walls are perforated in order to generate an AV fistula. In contrast, the intended arterial catheter serves as a passive source of reinforcement, of alignment, and of abutment intravascularly. Due to these different functions and construction features, the details of each catheter in the pair will be described in detail independent from the other.

The Construction And Organization of the Venous Catheter

The essential component parts and their interrelationship is illustrated by FIGS. 4-8 respectively. As seen therein, FIG. 4 shows a hollow introducer cylinder 20 which is a thin wall tube having a large diameter internal lumen 22. The proximal end 24 is configured as a locking arrangement 26 comprising two anti-rotation support bars 28, 30, an interlocking notch 32, and a flat interlocking surface 34. The internal lumen 22 extends through the entirety of the locking arrangement 26. In comparison, the distal end 36 terminates as a planar surface 38 and contains a cutout slot 40 in the tubular wall of the introducer cylinder 20. The internal lumen 22 extends through the planar surface 38 at the distal end 36; and the cutout slot 40 exposes a portion of the internal lumen volume to the ambient environment.

A component part of the venous catheter is the internal obturator shown by FIG. 5. An obturator, by definition, is a structure which closes or stops up an opening such as a foramen or internal lumen. As illustrated within FIG. 5, the obturator 50 is an extended rod-like hollow shaft of fixed axial length but having an external shaft diameter which is slightly smaller in size than the internal lumen 22 of the introducer cylinder 20 of FIG. 4. The obturator 50 has a small diameter internal lumen 52 which continues axially from the proximal end 54 to the distal end 56. The proximal end 54 is purposely configured as a semi-circular disc 58 having a extended finger portion 60. The small diameter internal lumen 52 of the obturator 50 extends through the semi-circular disc portion 58 as shown. In comparison, the distal end 56 terminates as a tapered end tip 62 and contains a portal 64 of sufficient size for a conventional guidewire to pass there through into the lumen 52.

It is intended and expected that the obturator 50 of FIG. 5 will be fitted into the proximal end 24 of the introducer cylinder 20 (illustrated by FIG. 4) and be extended through the large diameter internal lumen 22 along the entire axial length to form a cylinder-obturator composite as shown by FIG. 6. As seen therein, the locking arrangement 26 at the proximal end of the introducer cylinder 20 interlocks with the extended finger 60 and semi-circular disc 58 of the obturator 50 to form a composite proximal end 70. Similarly, the distal tapered end tip 62 of the obturator 50 passes through the distal end 38 of the cylinder 20 to form a composite distal end 72.

Note that in this composite orientation illustrated by FIG. 6, the small diameter internal lumen 52 of the obturator 50 is longer in axial length than the large diameter internal lumen 22 of the introducer cylinder 20; and that the cutout slot 40 of the introducer cylinder 20 exposes the obturator distal end 62 to the ambient environment at the composite distal end 72. Moreover, the portal 64 of the obturator 50 passes through the planar surface 38 of the introducer cylinder 20 and extends into the ambient environment with the concurrent exposure of the distal tapered end tip 62 and the portal 64 beyond the composite distal end 72.

The cylinder-obturator composite of FIG. 6 is the article to be percutaneously introduced into a peripheral vein and is to be extended intravenously through the peripheral vein until a desired location is reached. The percutaneous introduction is achieved typically by positioning a guidewire in the desired vein, utilizing percutaneous venipuncture, guiding catheters, fluoroscopy, and contrast venography. The back of the guidewire is first passed through the portal 64 at the distal end tip 62 and then passed through the internal lumen 52. The entire cylinder-obturator composite is then extended over the guidewire into the vein. The guidewire introduced at the portal 64 will travel over the entire axial length of the internal lumen of the obturator and exit at the composite proximal end 70 in a conventionally known manner. The cylinder-obturator composite is then extended intravascularly using the guidewire as the means for extension through the vein. In this manner, the obturator acts as a support vehicle and stiffening rod for the venous catheter during initial introduction and placement of the catheter in the vein.

When a vascular site is chosen which is deemed suitable for use, the entirety of the obturator 50 is removed from the internal lumen 22 of the introducer cylinder 20. The obturator of FIG. 5 is then to be entirely replaced and be substituted for by the tubular cutting tool illustrated by FIGS. 7 and 8 respectively. FIG. 7 shows the entirety of the tubular cutting tool as configured for this preferred first embodiment; and FIG. 8 shows particular details and individual structures existing at the distal end of the cutting tool.

As shown in FIG. 7, the tubular cutting tool 80 is an extended hollow tube 82 whose external diameter is sized to be only slightly smaller than the internal lumen diameter 22 for the introducer cylinder 20 of FIG. 4. The tubular cutting tool 80 itself has a small bore internal lumen 84 whose volume provides several capabilities. In part, the internal lumen 84 serves as a communication passageway for carrying an actuation wire 86 which is inserted at the proximal end 88 and conveyed via the internal lumen 84 to the distal end 94 of the cutting tool 80. The actuation wire 86 is employed by the physician to activate the vascular wall perforation capability on-demand. In addition, the internal lumen 84 serves as a volumetric passageway for the conveyance of pressurized carbon dioxide gas from the proximal end 88 to the distal end 94. A gas conduit 85 is attached to and lies in fluid flow continuity with the internal lumen 84 at the proximal end 88. A source of pressurized carbon dioxide gas (not shown) is controlled by a stopcock 87 which introduces a flow of pressurized carbon dioxide gas at will into the volume of the internal lumen 84 for conveyance to the distal end 94. An aperture 97 in the tubular cutting tool 80 at the distal end 94 provides for egress of the pressurized carbon dioxide gas after being conveyed through the internal volume 84.

Note also that the proximal end 88 is configured as an oval disc 90 having a rib 92 extending therefrom. The proximal end 88 thus forms part of an interlocking system suitable for engagement with the locking arrangement 26 of the introducer cylinder 20 illustrated previously by FIG. 4 herein. The radiopaque components of the cutting tool are non-axisymmetric which allows the polar (rotational) orientation of the cutting tool-introducer cylinder composite to be determined fluoroscopically. The cutting tool-introducer cylinder composite can then be rotated by manipulating the proximal end to adjust polar orientation.

Figure 8:
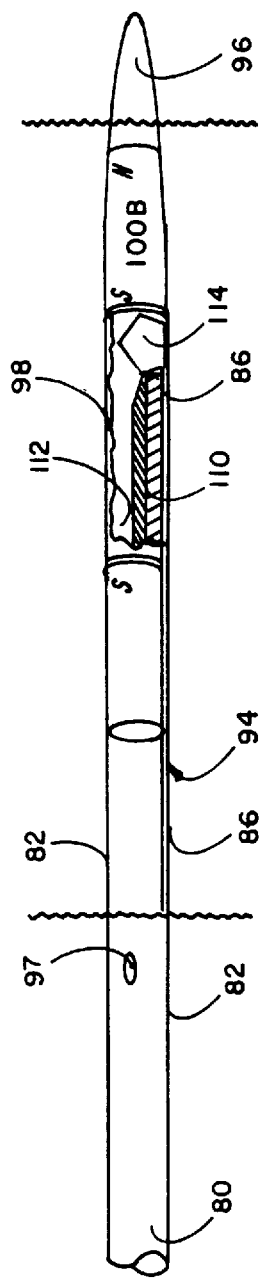
FIG. 8 is a partial sectional view of the distal end of the tubular cutting tool of FIG. 7.

FIG. 8 (as a cutaway view) reveals the details of the distal end 94 of the tubular cutting tool 80. The distal end 94 has three specific parts: a tapered end tip 96; vascular wall perforation means 98; and first and second magnet means 100a and 100b positioned adjacent to and in axial alignment with the vascular wall perforation means. It will be recognized and appreciated that (as shown within FIG. 8) the vascular wall perforation means 98 is situated near the tapered end tip 96 and is flanked by first and second magnet means 100a and 100b. However, the placement and ordered sequence of the magnet means 100a and 100b and the vascular wall perforation means 98 can be altered and interchanged in location as acceptable variations to the ordered sequence of parts presented by FIG. 8. Furthermore, a single magnet means rather than use of a pair is acceptable as another variation of the construction and structure.

In addition, it will be seen that the actuation wire 86 extends from the proximal end through the lumen 84 to the distal end 94 and connects with the vascular wall perforation means 98 such that the perforation mechanism can be activated at will and on-demand by the physician retaining possession of the proximal end of the tubular cutting tool 80 which remains exposed to the ambient environment outside the skin.

FIG. 8 also reveals several notable features about the magnet means 100a and 100b and the vascular wall perforation means 98 respectively. The magnet means are housed within and contained by the tubular wall of the cutting tool 80 entirely. The magnet means are desirably rare earth magnets or electromagnets having sufficient magnetic power and strength to attract and align another source of magnetic attraction such as a second catheter with the magnetic properties in-vivo. The magnet means may be a solid rod or a configured bar of matter within the lumen of or integral to the tubular wall of the cutting tool. While the actual dimensions may vary widely and radically, a typical rare earth magnet will be configured as a cylindrical mass 8–10 mm in length and 2–3 mm in diameter. The magnetic means are firmly embedded within the interior of the tubular cutting tool and will not shift or change position or orientation after the tubular cutting tool 80 has been manufactured and completely assembled.

Note also that the vascular wall perforation means of FIG. 8 rests completely within the interior volume of the cutting tool in the passive state but is elevated to become exposed to the ambient environment in the activated state. As is shown within FIG. 8, a fenestration 112 permits ambient exposure of a perforating mechanism through the tubular wall of the cutting tool 80 via elevation onto a tracked template 110 which escalates the perforation mechanism to a greater height from within the interior of the cutting tool 80. The particular perforation mechanism illustrated within FIG. 8 is shown as a sliding electrode 114 through which radiofrequency cutting current is passed.

The means by which the perforation mechanism is activated and placed in appropriate elevated position to achieve perforation is shown by FIGS. 9A–9D respectively. The actuation wire 86 provides the physician with the point of control. As the actuation wire 86 is pulled by the attending physician at the proximal end, the sliding electrode 114 is elevated and moves along a set track on the template 110. The non-linear geometry of the track causes the electrode 114 to protrude through the fenestration 112 and become exposed to the ambient environment over the entire length of the template distance. Subsequently, when the actuation wire is advanced towards the distal end, the electrode 114 travels in the reverse direction and returns to its original position within the interior of the tubular cutting tool 80. In this manner, the attending physician can activate and inactivate the perforation means at will; and cause the sliding electrode 114 to become exposed as a consequence of moving along a set track and distance; and then to subsequently withdraw and reverse its direction of travel such that it becomes enclosed again and protected by the tubular wall of the cutting tool 80.

During the activation of the sliding electrode 114, a radiofrequency alternating current of predetermined amplitude ($\alpha$) and frequency (f) is applied to the electrode and conducted through actuation wire 86 with a complimentary electrode disposed within the arterial catheter serving as the ground. The radiofrequency current traveling from the elevated electrode 114 in the tubular cutting tool 80 to the complimentary electrode in the arterial catheter thus is the active cutting force which creates a perforation through the vascular walls on-demand. To provide sufficient and readily available radiofrequency current when and as required, a conventional electrosurgical console (such as a BOVIE, BARD, or VALLYLAB console) is preferably used as a power source.

Concurrent with electrode activation, the attending physician will also open the stopcock 87 and allow a flow of compressed carbon dioxide gas ($CO_2$) into the tubular cutting tool 80. Preferably an electrically actuated solinoid (not shown) is used to release a burst of compressed $CO_2$ gas from the pressurized tank in synchrony with the application of the radiofrequency current. The released burst of the compressed $CO_2$ is delivered through the gas conduit 85 into the internal lumen 84, where it travels through the interior of the cutting tool 80 to the aperture 97, and exits through the aperture 97 into the vein lumen. The volume of $CO_2$ gas exiting the aperture 97 transiently displaces the venous blood in the area of the fenestration 112 during the radiofrequency activation of the sliding electrode 114, a highly advantageous circumstance. Blood is an aqueous, electrolyte-rich fluid which conducts electrical current readily. As such, the temporary displacement of blood by $CO_2$ in the vein lumen (and after perforation in the arterial lumen as well) at the selected anatomic site is desirable to obtain sufficient electrical current density at the point of electrode contact to cleanly incise and penetrate through the vascular walls.

The complete venous catheter suitable for activation on-demand and for generating an AV fistula is shown by FIG. 10. Clearly, the insertion of the tubular cutting tool 80 into the internal lumen 22 of the external cylinder 20 in a locked arrangement provides the venous catheter suitable for use in-vivo. The cylinder-cutting tool composite of FIG. 10 is the complement and counterpart of the cylinder-obturator composite of FIG. 6. However, the functions of each composite construction are markedly different. Thus, whereas the cylinder-obturator composite of FIG. 6 provides a highly desirable catheter for percutaneous introduction and extension intravenously through a peripheral vein to a specific location or chosen anatomic site, the cylinder-cutting tool composite of FIG. 10 provides the alignment and specific placement intravenously at a chosen anatomic site within the vein as well as providing the physical mechanism and means by which to perforate the vascular walls of closely associated veins and arteries concurrently. In addition, the radiopaque non-axisymmetric components allow fluoroscopic identification and manual adjustment of polar (rotational) orientation of the cutting tool-introducer cylinder composite.

The Construction and Organization of the Arterial Catheter

The arterial catheter is a long, flexible hollow tube having a fixed axial length, a discrete proximal end, a discrete distal end, and at least one internal lumen of predetermined volume as is illustrated by FIG. 3 herein. Typically, the axial length will vary in the range from about 40–150 centimeters and the external diameter of the hollow tube will often be in the range from about 1.5–2.5 millimeters in size. While the proximal end of the arterial catheter is conventional in most respects, the internal lumen of the catheter is preferably joined to and lies in fluid communication with a source of compressed carbon dioxide gas ($CO_2$) in a manner similar to that previously described herein for the proximal end of the venous catheter. Thus, compressed $CO_2$ gas is released on-demand from a pressurized tank; is delivered via a gas conduit into the internal lumen; and travels through the linear volume of the internal lumen to a distal aperture through which the $CO_2$ gas exits into the arterial lumen in-vivo. The volume of $CO_2$ gas exiting the catheter displaces at least some of the arterial blood in the anatomic area of the electrode; and maintains the radiofrequency electrical current density at the point of contact between the radio frequency electrode and the vascular tissue. This will facilitate clean incision of the vascular walls.

The distal end of the arterial catheter is unique in structure, construction, and organization. A detailed showing of the distal end is provided by FIG. 11. As shown by FIG. 11, the arterial catheter 200 has a distal end 212 which is divided into four individual segments in series. Farthermost is the tapered distal end tip 224 having portals 226 and 210 and non-axisymmetral lumen 227 for externalized passage of a guidewire there through; and an aperture 234 for the egress of compressed $CO_2$ gas into the arterial lumen. The tapered distal end tip 224, the portals 226 and 210, and the lumen 227 thus serve as and are adapted for intraarterial guidance of the arterial catheter externally over a guidewire and through a blood vessel in-vivo to a chosen anatomic site. In contrast, the aperture 234 is in direct communication with the axial internal lumen 214 and allows the passage of compressed $CO_2$ gas through the catheter interior with egress via the aperture. This facilitates the creation of the AV fistula by displacement of arterial blood on-demand at the chosen anatomic site.

Positioned adjacent to the tapered distal end tip 224 are a pair of rare earth magnets 228a and 228b which serve as the magnet means for this embodiment. The rare earth magnet pair 228 is set in axial alignment with the distal end tip 224 and has sufficient magnetic power and strength to cause an adjustment in intraarterial catheter position when placed in proximity with the magnet means of the venous catheter described previously herein.

The fourth structure is the fixed electrode 230 which serves as the electrical ground for the radiofrequency circuit; and which is positioned adjacent to and flanked by the rare earth magnet pair 228 and which is set in axial alignment with the tapered distal end tip 224 of the arterial catheter 200. The arterial electrode 230 provides intravascular support for a chosen portion of the arterial wall and completes the radiofrequency circuit during the perforation process in-vivo in order to generate an AV fistula. The remainder of the hollow tubular wall 202 and the axial internal lumen 214 are as previously described.

Since magnetic interaction is deemed essential to the proper function of the arterial catheter, the magnetic means preferred in this embodiment is the use of two rare earth magnets which will provide sufficient magnetic power to cause an intravascular adjustment in position for the arterial catheter when in proximity to the magnetic means of the venous catheter in-vivo. Desirable magnetic materials for use as magnet means thus include the neodymiun-iron-boron compositions and cobalt-samarium compositions. Alternatively, an electromagnet can be substituted in place of a rare earth magnet composition as a desirable magnetic means. In addition, any other source of magnetism which can be demonstrated to provide sufficient magnetic power (as conventionally measured and determined in Gauss) may be employed and positioned as an effective and useful substitute.

In comparison, the arterial electrode has two specific functions in-vivo: To provide a physical source of reinforcement and support during the process of perforating both the venous and arterial vascular walls concurrently; and to provide a grounding terminal for completion of the radiofrequency electrical circuit. The electrode may therefore be composed of any non-ferrous conductive matter such as carbon, copper, zinc, aluminum, silver, gold, or platinum.

Alternative Catheter Embodiments And Formats

In the preferred embodiment of the catheter apparatus, both the venous catheter and the arterial catheter comprise electrodes; and the active force for transvascular perforation of the closely associated vein and artery at a chosen anatomic site is via the transmission of a radiofrequency electrical current at a predetermined amperage and frequency from the electrode embedded in the aligned venous catheter through both vascular walls to the grounding electrode within the aligned arterial catheter. The use of radiofrequency electric current, however, is only one means for perforating the vascular walls of a closely associated vein and artery in order to generate an AV fistula in-vivo.

In an alternative embodiment of the vascular wall performation means disclosed in detail hereinafter, a static discharge electrical spark is used to perforate the vascular walls between the electrode in the venous catheter and the electrode in the arterial catheter. The electrodes in this alternative format would differ little in design and structure from those depicted in the preferred embodiment. Moreover, the displacement of venous (and arterial) blood by the introduction and subsequent release of compressed $CO_2$ gas through the catheter internal lumen in this alternative embodiment would also desirably occur as described for the preferred embodiment previously herein; but this usage and feature is optional and is not a necessary adjunct to the process of vascular wall perforation and AV fistula formation created by the use of a static electrical spark between the electrodes.

In still another embodiment of a useful catheter construction, the vascular wall perforation means can take form as a microscalpel of conventional design which may be elevated from and subsequently recessed back into the internal volume of the tubular cutting tool at the distal end using the fenestration and the tracked template of the venous catheter described previously for the preferred embodiment. The microscalpel is used mechanically to incise and bore into the vascular walls without the aid of electrical current. The venous cutting tool is structurally similar to that disclosed as the preferred embodiment with the exception that the sliding electrode has been replaced by a sliding microscalpel, which is similarly activated on-demand by the physician using the actuation wire. In this microscalpel embodiment, however, the presence of compressed $CO_2$ gas at the anatomic site chosen for AV fistula formation has no advantage; consequently, the gas conduit, the stopcock, and the source of pressurized $CO_2$ gas as components of the venous catheter are unnecessary and redundant. Furthermore, in this microscalpel construction format, the electrode disposed at the distal end of the arterial catheter in the preferred embodiment is now replaced and substituted by an abutment block (or anvil) segment which is positioned adjacent to and is flanked by at least one or a pair of rare earth magnets for catheter alignment as previously described. The placement and orientation of the abutment block is similar to that shown for the grounding electrode in the preferred arterial catheter construction; but the abutment block is typically a cylinder or rod composed of hard and generally non-conductive, resilient matter which will provide firm support during the vascular wall perforation process; and also serve to confine the microscalpel cutting action to penetrating only a small and limited area of arterial vascular wall at the chosen anatomic site—thereby preventing excessive vascular injury. The range of resilient materials suitable for the abutment block thus include hard rubbers, plastics such as LEXAN or PLEXIGLASS polymers, polycarbonate compounds, vinyl polymers, polyurethanes, or silicon-based compositions.

The Functional Relationship Between the Venous Catheter and the Arterial Catheter Both the venous catheter and the arterial catheter comprise unique features at their respective distal ends which will provide proper alignment in-vivo in order that a AV fistula can be generated on demand. Clearly, it is envisioned and intended that the venous catheter will be percutaneously introduced and extended through a peripheral vein until a desirable anatomic location is reached. Similarly, it is expected that the arterial catheter will be percutaneously introduced into and extended through a closely associated peripheral artery until both the arterial catheter and the venous catheter lie in adjacent position, each within its own individual blood vessel. A representation of this adjacent positioning between the preferred arterial catheter and the venous preferred catheter is illustrated by FIG. 12.

Figure 12:
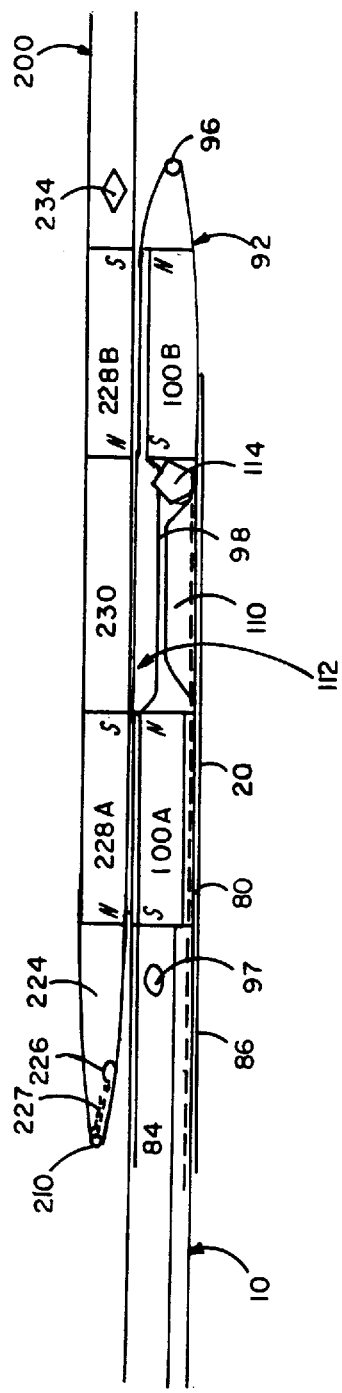
FIG. 12 is a partial sectional view of the preferred venous catheter of FIG. 2 and the preferred arterial catheter of FIG. 3 in proper parallel alignment as a consequence of magnetic attraction and interaction.

As shown within FIG. 12, each of the preferred catheters individually will rest intravascularly within its own blood vessel (which has been deleted from the figure for purposes of clarity) and lie in parallel alignment as a consequence of the magnetic attraction between the pair of rare earth magnets 228a and 228b of the arterial catheter 200 and the opposite pair of rare earth magnets 100a and 100b of the venous catheter 10. The magnetic attraction between these four rare earth magnets is of sufficient magnetic power to cause intravascular adjustment in position for the venous catheter 10 and the arterial catheter 200 lying within their individual, but immediately adjacent, blood vessels. The magnetic attraction and force is thus a transvascular effect and result whereby the magnetic field affects each of the catheters lying individually and separately in different but closely associated blood vessels.

It is also important to note the orientation effect and overall alignment pattern created as a consequence of transvascular magnetic attraction. The venous catheter is shown as extending in a easternly direction such that the perforation means 98 (including the sliding electrode 114, the elevating template 110 and the fenestration 112) are in proper position and flanked by the pair of the rare earth magnets 100a and 100b. In comparison, the arterial catheter 200 lies in an westernly direction such that the arterial catheter body is brought into aligned position over the distal end tip 96 of the venous catheter 10; and consequently, that the grounding electrode 230 of the arterial catheter 200 is brought directly into generally parallel alignment with the vascular wall perforation means 98 of the venous catheter 10. In this manner, the grounding electrode 230 of the catheter then lying within the peripheral artery becomes closely associated and in proper alignment with the sliding electrode 114 of the venous catheter 10 then lying with the peripheral vein. The only intervening matter existing in-vivo is thus the thickness of the peripheral vein wall, the thickness of tissue between the closely associated vein and artery, and the thickness of the arterial wall itself. In correctly chosen anatomic sites, the sum of these three thickness layers will typically be less than 3 mm in total distance. The sliding electrode (or other vascular wall perforation means) can then be activated on-demand and at will with substantial certainty that the physical action of perforating both the venous and arterial vascular walls can be achieved with minimal injury to the blood vessels and with a minimal loss of blood volume into the surrounding tissues.

It is essential to recognize and appreciate, therefore, that it is the magnetic attraction between the rare earth magnets positioned in advance and set in axial alignment within each of the venous and arterial catheters individually which creates the phenomena of transvascular magnetic attraction and interaction and which generates sufficient force such that the individual catheters lying in adjacent blood vessels will move in axial position as a consequence of the strength of the magnetic interaction. Moreover, each catheter will move more readily with its respective vessel lumen to apply compressive force; and in so doing, minimize the distance between the radio frequency electrode and the sliding electrode. The grounding electrode of the arterial catheter and the sliding electrode of the venous catheter are similarly aligned and set in advance within each of the respective catheters such that when the transvascular magnetic attraction occurs and each of the catheters individually move into position as a consequence of magnetic attraction, the vascular wall perforation means will then be in proper parallel alignment to generate an AV fistula on demand in a safe and reliable manner.

B. An Alternative Embodiment Of The Catheter Apparatus

An alternative embodiment of the present invention provides a pair of catheters which are used in tandem for generating an AV fistula on-demand between a closely associated artery and vein at a chosen vascular site in-vivo. Each of the individual catheters constituting the pair are structurally similar except for a few detailed features.

For purposes of description and detail, a single catheter of the pair will suffice. Accordingly, all which pertains to the description of one catheter applies completely to the construction, structure, and features of the other catheter constituting the pair. Each catheter comprises one hollow tubular wall having a fixed axial length, a discrete proximal end of conventional manufacture and design, a unique discrete distal end, and provides two internal lumens (of unequal diameter and predetermined size) which extend coaxially and substantially in parallel over the axial length of the tubular wall. Since the structural features of distinction exist primarily at the distal end of each catheter, this detailed disclosure will focus and emphasize these unique structures and features.

The distal end of the dual lumen catheter intended to be used in pairs for generating an AV fistula are illustrated by FIGS. 13, 14, and 15 respectively. FIG. 13 provides an overhead view of the catheter at the distal end; in comparison, FIG. 14 provides an axial-section view of the catheter distal end while FIG. 15 provides a cross-sectional view of the catheter taken along the axis Y Y'.

As shown by FIGS. 13–15, each of the catheters 300 comprises a tubular wall 302 which terminates at the distal end 304 as an end tip 306 adapted for passage of a guide wire and for intravascular guidance via portals 305 and 309 and non-axisymmetric lumen 307 through a blood vessel in-vivo to a chosen vascular site. Within the tubular wall 302 are two internal lumens 308, 310. The first internal lumen 308 extends from the proximal end of the catheter (not shown) and terminates at the distal end 304 as a portal 312. The diameter of this first internal lumen 308 is relatively large; and this first internal lumen is intended to carry a variety of fluids such as liquid contrast medium for radiological purposes and pressurized gases as $CO_2$ for displacing blood at the chosen anatomic site. The second internal lumen 310 extends from the proximal end of the catheter (not shown) as a relatively small bore tube and terminates at the distal end tip 306 where a fixed electrode 320 is imbedded. The second internal lumen 310 thus serves as the conduit for an electrical lead 322 which is carried from the proximal end of the catheter through the catheter mass via the second internal lumen 310 and ends at the distal end tip 306 at the embedded electrode 320.

Note that the fixed electrode 320 is joined to the electrical lead 322 which is in electrical communication with a source of electrical energy (not shown) capable of producing a static electrical charge on command. The electrode 320 is typically formed of solid, electrically conductive metal. The electrode 320 comprises at least two component parts: an electrical supporting unit 324 which is embedded in the material of the catheter wall and firmly fixed in position within the catheter mass; and an extending discharge spike 326 which extends from the support unit 324 through the thickness of the catheter wall material and terminates in the ambient environment. As an electrical system, a static discharge from the electrical source is introduced through the catheter via the electrical lead 322 and conveyed to the electrode 320 on demand. The electrical current is conveyed to the supporting unit 324 and the charge is then discharged through the spike 326 from the interior of the catheter into the external ambient environment as a static electrical spark of predetermined magnitude.

Positioned adjacent to the electrode 320 and set in fixed alignment at the distal end tip 306 is a rare earth magnet 330 (or, alternatively, other magnet means). This rare earth magnet is configured desirably as a rectangular block of magnetic metal formed of neodymium-iron-boron alloy and/or cobalt-samarium alloy. Note also that the orientation of the magnetic attraction in terms of the "north" and "south" polarity is known and identifiable. The rare earth magnet thus serves as magnet means positioned at the distal end and set in axial alignment at the distal tip of the catheter. In addition, an optional second rare earth magnet 332 may be set in fixed alignment to flank the electrode 320. The optional second rare earth magnet 332 is desirably identical in configuration and composition to the magnet 330; and provide added magnetic force for alignment. These magnet means have sufficient attractive force to cause an adjustment in position for the catheter in-vivo when placed in proximity with another source of magnetic attraction disposed within a closely associated (and preferably adjacently positioned) blood vessel.

In comparison it will be recognized that the electrical lead 322, the electrode 320, the supporting unit 324 and the discharge spike 326 collectively constitute the vascular wall perforation means for this embodiment. Note that the entire electrical current carrying and spike discharge apparatus constituting the vascular wall perforation means are positioned adjacent to at least one rare earth magnet (the magnet means) of the catheter and are set in axial alignment with the distal end tip of the catheter. Thus, when there is a magnetic interaction involving the rare earth magnet 330 (and optionally the rare earth magnet 332), this static electrical system will become intravascularly adjusted in position in-vivo; and the static discharge will serve as the means for perforating the vascular walls at will whenever sufficient potential is applied to the two electrodes to generate an AV fistula.

Figure 16:
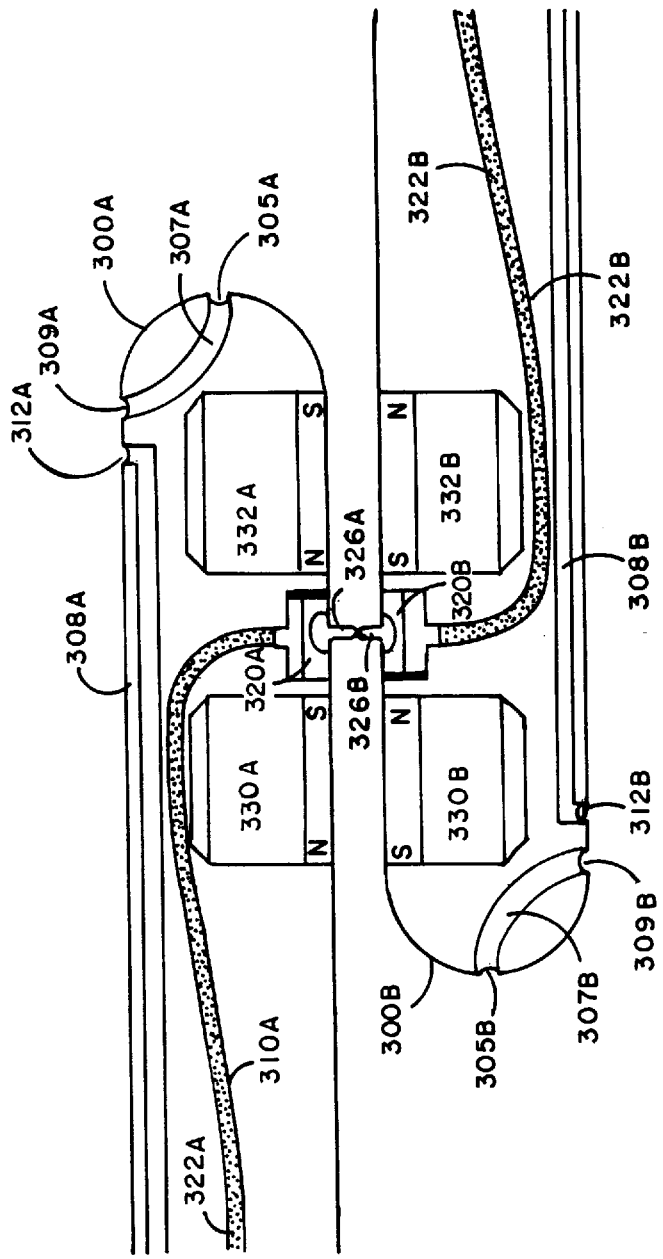
FIG. 16 is an axial-section view of a pair of alternative embodiment catheters in proper parallel alignment for generating an arteriovenous fistula.

The intended manner of usage under in-vivo conditions is illustrated by FIG. 16. For purposes of clarity the first catheter 300a is presumed to be in a peripheral vein whereas the second catheter of the pair 300b is envisioned as being within a peripheral artery. The vascular walls have been deleted from the figure to demonstrate the working relationship between the two catheters in tandem and the mechanism by which an AV fistula is generated using this catheter apparatus.

As shown by FIG. 16, the only difference between the first catheter 300a and the second catheter 300b is the polarity and polar orientation of the rare earth magnets 330a, 330b (and optionally rare earth magnets 332a, 332b). Recalling also that each catheter has been placed within the confines of an individual blood vessel constituting a closely associated peripheral artery and vein, it is clear that the opposite polarity in each rare earth magnet will attract the catheters towards each other. Thus, a transvascular magnetic attraction occurs which not only moves each of the catheters 300a, 300b individually within its own blood vessel in a manner which brings the pair closely together, but also the strength of the magnetic attraction is sufficiently great in power (Gauss) that the rare earth magnets are drawn and aligned to each other in parallel positions as shown within FIG. 16. The consequence of this transvascular magnetic attraction and alignment in parallel between individual catheters disposed in separate blood vessels independently causes the electrodes 320a, 320b and the discharge spikes 326a, 326b to become closely placed and aligned in parallel. It is also desirable in practice to ascertain that adequate alignment by magnetic attraction has occurred and that a suitably small distance occurs between the individual discharge spikes by measuring the electrical resistance between the electrical contacts 320a, 320b. Fluoroscopy confirms appropriate catheter position, alignment, and polar (rotational) orientation.

After the determination of adequate alignment is made, the source of static electrical discharge is engaged, and the electrical charge is conveyed to the electrode discharge spikes. A static electrical charge is accumulated, discharged and passed from one of the spikes 326a to the other aligned spike 326b, thereby completing the electrical circuit. In so completing this electrical circuit, the electrical spark vaporizes portions of the vascular wall for both the vein and the artery at the same moment. The arcing spark vaporizes vascular tissue and creates a perforation in common between the blood vessels. Blood in the artery rushes through the perforation in the arterial wall into the aligned hole of the perforation in the vascular wall of the adjacently positioned vein. In this manner, the AV fistula is generated safely, reliably, and on-demand.

It will be noted and appreciated that this alternative embodiment of the catheter apparatus can also employ other vascular wall perforation means than a static electrical discharge to perforate the vascular wall. An immediate and easily available substitution and replacement for the entire electrical lead, electrode, and discharge spike—the perforation means—is the use of a fiber optic cable and a source of laser (light) energy. The fiber optic cable (comprised of multiple fiber optic strands) is conveyed through the internal lumen and passes through the tubular wall material of the catheter at the distal end tip to terminate as a fiber optic end surface exposed to the ambient environment. The fiber optic cable would then transmit and convey laser (light) energy from the energy source on-demand as the means for perforating the vascular wall of the closely associated blood vessels. Also, the catheter lying in the adjacent blood vessel would serve to diffuse the applied laser energy and prevent injury to the opposite vascular wall.

V. An Illustrative Method For Creating An AV Fistula In-Vivo Using The Preferred Embodiment To demonstrate the methodology employing a catheter apparatus to generate an AV fistula between a peripheral artery and an adjacent vein, it is desirable to focus upon and utilize a specific anatomical area in the extremities of a living patient as an illustrative example. For this illustrative purpose lone, the description presented hereinafter will emphasize and be limited to the creation of an AV fistula between the radial or ulnar arteries and a closely associated and adjacently positioned vein in the distal forearm. It will be expressly understood and recognized, however, that this illustrative description is merely representative of such procedures generally; and is but one example of the many different and diverse instances of use which can be reproduced in many other anatomical areas of the body at will and on-demand. Under no circumstances, therefore, is the present invention and methodology to be or restricted to the particular anatomic sites described or limited to the particular embodiment of the catheter apparatus employed.

The illustrative example presented below employs the preferred embodiment of the catheter apparatus described in detail previously herein. Clearly, although this preferred embodiment is deemed to be an advantageous construction and the best mode structure developed to date, all other alternative embodiments of the catheter apparatus—regardless if used singly or in pairs—are also deemed to be suitable and appropriate for use in a manner similar to that described below. In addition, given the wide range and diversity of structural components, design features and format variations in catheter construction which have already been disclosed herein and are within the scope and breadth of the present invention, it will be understood that certain minor changes in the procedural details and modes of use may be necessary which differ from the preferred methodology.

Initially, and most importantly, it will be recognized and appreciated that the methodology is intended to be performed in the angiography suite of a hospital by thoroughly trained and experienced invasive radiologists. The reader is presumed to be familiar with the common procedures performed by invasive radiologists today; and no attempt will be made herein to familiarize or acquaint the reader with the conventional techniques of ultrasound imaging, fluoroscopy and fluoroscopic imaging, and other radiological techniques for contrast imaging. The reader is also presumed to be familiar with general procedures of catheterization and especially with the modified Seldinger technique reviewed in detail previously herein. Finally, to aid the reader in becoming acquainted with the essence of the methodology and in order to appreciate its importance and major advantages, FIGS. 17–26 are included; and direct reference and comparison of these figures will aid in ease of understanding and full comprehension of the methodological details.

Figure 17:
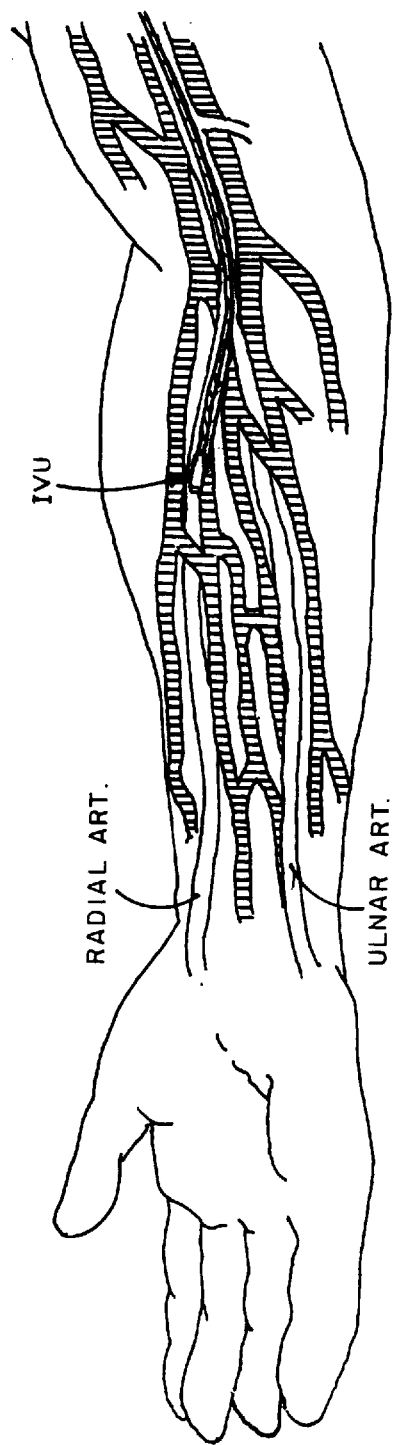
FIG. 17 is an illustration of the vascular system in the human forearm in which an intravascular ultrasound probe has been extended into the radial artery.

The first step in the methodology involves obtaining percutaneous arterial access to a suitable peripheral artery (such as the radial or ulnar arteries) in the forearm through the brachial artery or, less desirably, the common femoral artery. An introducer sheath is placed into the brachial artery using conventional techniques described extensively in the medical literature. The sheath is placed at mid-bicep and directed distally towards the hand. An intravascular ultrasound probe (hereinafter "IVU") is then introduced over a guidewire into the forearm arterial blood vessels. This is shown by FIG. 17 which shows the intravascular ultrasound probe being passed antegrade into the radial artery.

Figure 18:
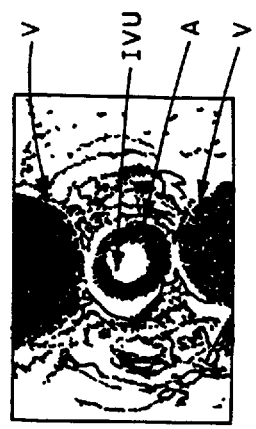
FIG. 18 is an illustration of an intravascular ultrasound-created image showing the radial artery wall and the adjacently positioned veins using the probe of FIG. 17.

The IVU provides circumferential ultrasonic visualization of structures in the immediate vicinity of the artery in which it is positioned as is illustrated by FIG. 18. As shown, FIG. 18 clearly demonstrates two large veins ("V") immediately adjacent to the radial artery ("A") at the position shown by FIG. 17. Veins in the forearm that lie in close proximity to the radial artery are readily identified. The echolucent blood in the veins stands out in sharp contrast to the relatively echogenic fibrous and fatty tissues and muscle which surrounds the veins themselves. Desirably, the IVU is passed through both the radial and ulnar arteries independently and in succession in order to note the location and position of those large diameter veins lying immediately adjacent to the artery. Commonly, several anatomical zones are present in the forearm of most patients where large diameter veins pass within one or two millimeters of these major peripheral arteries. From among these anatomical zones, one of these is selected for the generation of the AV fistula. Ideally, the chosen anatomical area should be fairly distal or peripheral in the forearm, as this will result in a greater number of veins being exposed to high volume flow and thus a greater number of potential access sites for percutaneous venipuncture. Because veins have unidirectional valves in them, veins distal to the AV fistula will not generally dilate.

Figure 19:
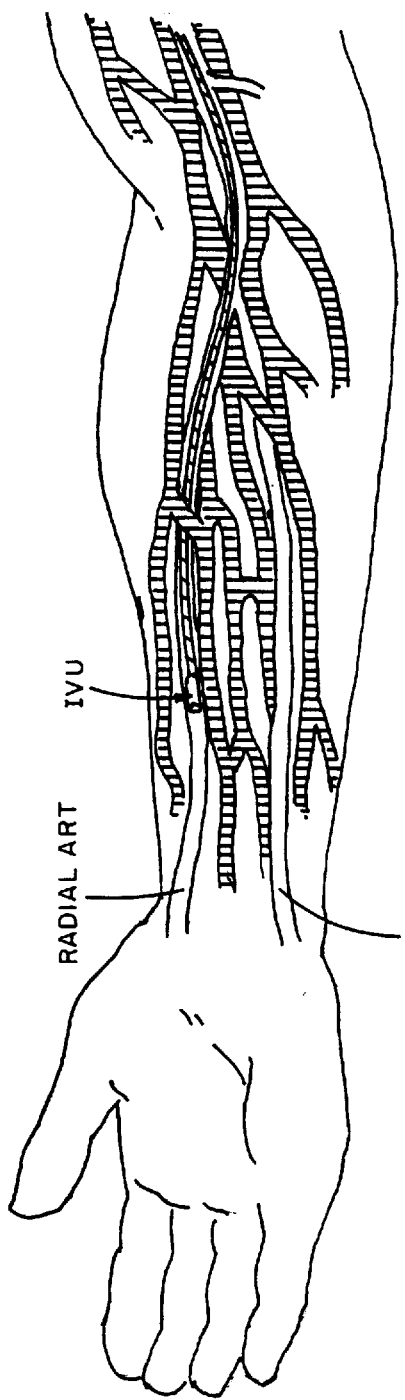
FIG. 19 is an illustration of an extended intravascular ultrasound probe within the radial artery at a site of arterial-venous proximity.
Figure 20:
FIG. 20 is an illustration of an ultrasound-created image showing the radial artery wall and immediately adjacent veins using the probe of FIG. 19.

This result is illustrated by FIG. 19 where the anatomic area is selected in the distal radial artery in the location where a sizable diameter vein lies immediately adjacent to the arterial wall. The chosen anatomic site is shown by the intravascular ultrasound image of FIG. 20 which reveals an adjacently positioned vein on one side of the radial artery lumen.

Figure 21:
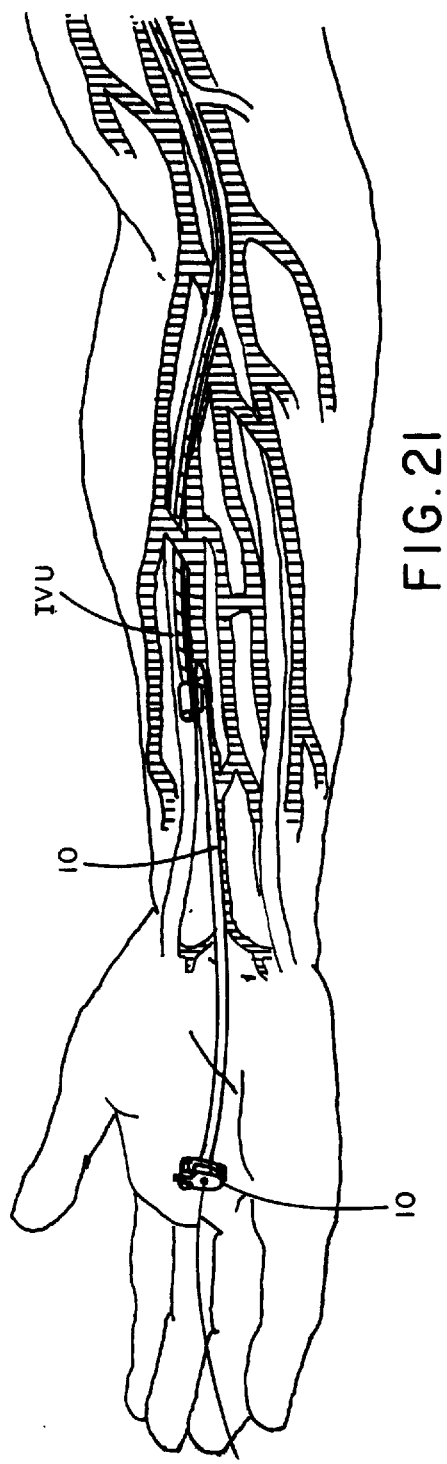
FIG. 21 is an illustration showing the percutaneous introduction of a venous cylinder-obturator complex and its placement near the ultrasound probe in the radial artery.
Figure 22:
FIG. 22 is an illustration of an ultrasound-created image showing the existence of the venous cylinder-obturator complexed in the selected vein at the site of arterial-venous proximity.

The second step is to obtain venous access for the venous catheter which takes form initially as the cylinder-obturator composite described previously herein. Percutaneous venous access is desirably obtained at the wrist. Fluoroscopic contrast venography is performed to define forearm venous anatomy. Under fluoroscopic guidance, a radiological guide wire is advanced through the percutaneous venous access to the chosen vein at the anatomic zone selected for generating the AV fistula in the forearm. The techniques required for this maneuver are conventional and fundamental to the practice of invasive radiology. This procedure is illustrated by FIGS. 21 and 22 respectively. Fluoroscopy shows the guidewire to be in close proximity to the IVU probe. In addition, as shown by FIG. 22, the extremely echogenic guidewire is easily visualized and imaged within the chosen vein lumen by IVU imaging. In this manner, the proper placement of the venous catheter in the chosen vein is inserted.

As shown by FIG. 21, the preferred venous cylinder-obturator composite 10 is introduced at the wrist and passed antegrade into the chosen vein over the previously placed guidewire. Fluoroscopy and intravenous contrast medium assist extension and guidance of the venous catheter through the vein; and a correct position is identified and placement confirmed for the venous catheter at the chosen site in the vein. Once again, IVU readily demonstrates the venous catheter within the lumen of a chosen vein.

It will be recalled that the venous catheter (the introducer cylinder-obturator composite format) measures 6–9 French (approximately 2–3 mm) in diameter; and typically will be about 40 centimeters in length. At the proximal ends the radiologist uses a handle to manipulate the venous catheter during placement. The venous catheter desirably employs the removable solid obturator during this phase in order to facilitate advancement of the venous catheter complex, preferably as described previously, the obturator has about a 0.2–0.5 mm internal lumen which extends coaxially down its central axis and allows the venous catheter complex to be passed coaxially over the guidewire into the proper position after the guidewire placement has been verified as correct.

Once good positioning and placement is verified and confirmed for the venous catheter (the introducer cylinder-obturator composite format), the IVU probe is removed and replaced with the arterial catheter 200 described previously herein. The construction of the arterial catheter provides substantial flexibility and offers a much longer axial length than its venous counterpart. Typically, the arterial catheter has an external diameter of about 5–7 French (approximately 1.5–2 mm in diameter) and has a typical length of about 100 centimeters to facilitate placement in an accessible artery. However, passing the positioned guidewire internally through the entire 100 cm length of catheter can be cumbersome and difficult. For this reason, the arterial catheter (much like the IVU probe) typically has a short-length, non-axisymmetric passageway or lumen which extends from the center of the distal end tip tangentially for about 1 cm distance and ends at the sidewall of the catheter about 1 centimeter from the distal end. This short non-axisymmetric lumen provides an externalized "monorail" mode of passage for the guidewire after insertion at the distal end tip; and allows the arterial catheter to be passed over the properly position guidewire without need for internally passing the guidewire through the entire axial length of the catheter. This "monorail" mode of externalized guidewire passage through a catheter is conventionally known, facilitates proper placement, and offers better control of the catheter for the radiologist when positioning the arterial catheter in-vivo.

Figure 23:
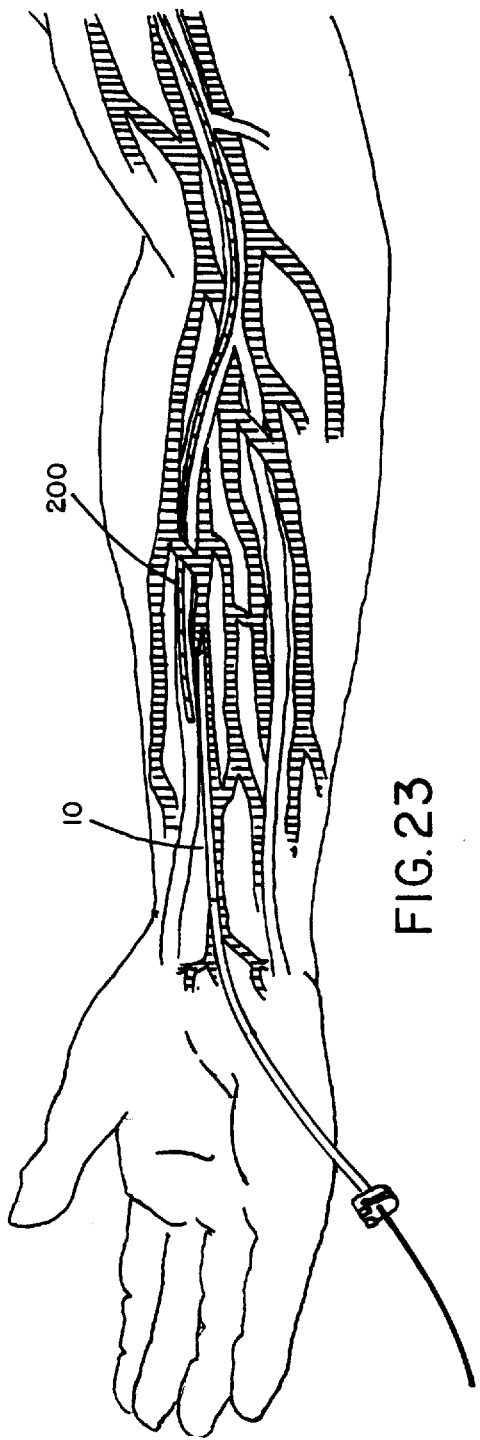
FIG. 23 is an illustration showing the venous catheter and the arterial catheter in the adjacent blood vessels under simulated in-vivo conditions.
Figure 24:
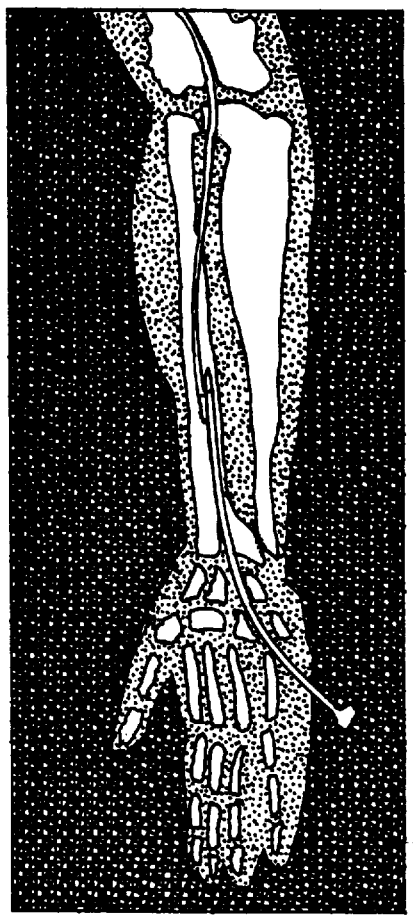
FIG. 24 is an illustration of a fluoroscopic-created image showing the alignment between the venous catheter and the arterial catheter of FIG. 23.

The manipulation and introduction of the arterial catheter is illustrated by FIGS. 23 and 24 respectively. As shown by FIG. 23, after the intravascular ultrasound probe has been removed, the arterial catheter is passed over the previously positioned guidewire, introduced into the artery, and advanced to the chosen anatomical site previously held by the IVU probe, Moreover, as illustrated by FIG. 24, fluoroscopy reveals when good and proper alignment exists between the positionings of the arterial catheter in relation to the venous catheter in the closely associated vein. Thus, under the fluoroscopic guidance, the arterial catheter is advanced over the guidewire into the radial artery to the chosen position previously occupied by the IVU probe.

After ascertaining that close proximity of the arterial catheter to the venous catheter exists, the relative positions are carefully adjusted under fluoroscopy such that the radiopaque markers on each of the catheters are carefully in alignment. In addition, radial radiopaque markers on the introducer cylinder allow rotational position to be adjusted fluoroscopically to insure correct orientation of the distal fenestration. Thus, when correctly aligned, the two catheters (each within its individual blood vessel) will overlap for an estimated distance of about 35 mm. If the overlapping distance does not appear to be adequate or if the radiologist is unsure that the two catheter tips are properly aligned, each of the catheters may be adjusted in position as long as needed in order to verify and confirm a proper alignment.

Figure 25:
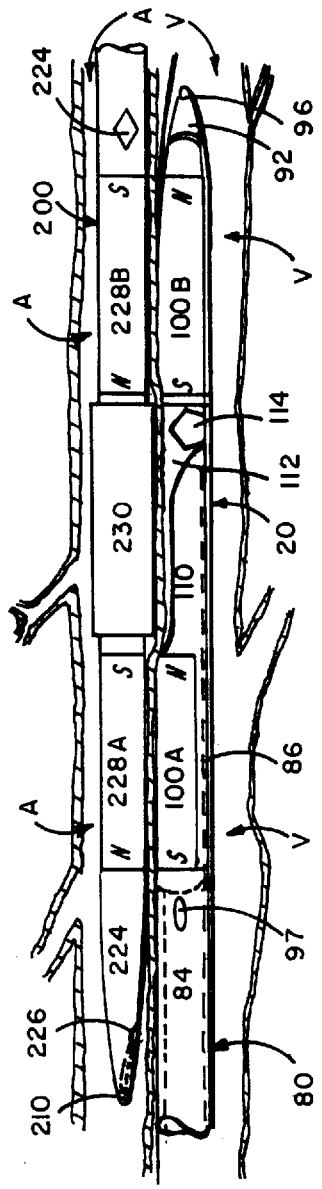
FIG. 25 is a sectional view of the alignment overlap between the distal end of the venous catheter and the distal end of the arterial catheter under simulated in-vivo conditions.

When, and only when, a correct and proper alignment has been made between the arterial and venous catheters in-vivo, the obturator component is removed from the venous introducer cylinder and replaced with the tubular cutting tool previously described. The tubular cutting tool is a semi-rigid rod with the same dimensions as the obturator and comprises the pair of rare earth magnets having the proper size and orientation to attract the rare earth magnets within the arterial catheter distal end. The magnetic attractive force will cause a transvascular attraction between the two opposing pairs of rare earth magnets; and the magnetic attractive force is of sufficient magnitude such that the arterial catheter and the venous catheter will adjust in position individually as a result and consequence of the magnetic interaction. This event and effect is illustrated by FIG. 25 in which the arterial catheter lying within the radial artery moves into proper alignment and precise positioning as a result of the magnetic interaction with the magnet means of the venous catheter lying within the adjacent vein. After this transvascular magnetic attraction and adjustment in position between the two catheters has occurred, the vascular wall perforation means at the distal end of the venous catheter may be activated at will and on-demand to generate the AV fistula at that precise location.

The preferred embodiment of the venous catheter 10 employed utilizes a radiofrequency electrode which slides in a controlled track upon a elevating template and which becomes exposed through a fenestration as a result of traveling over the template track. The sliding electrode is actuated by way of a sliding wire running the length of the tubular cutting tool; and the actuation wire is engaged preferably by a screw mechanism in the handle at the proximal end held by the radiologist. Once actuated, the electrode is moved along the curvilinear track on the elevating template resulting in the protrusion of the electrode through the fenestration into the exterior of the venous catheter. Simultaneously, radiofrequency current is delivered to the sliding electrode by way of the conductive actuation wire; and the grounding electrode in the arterial catheter completes the electrical circuit for vascular perforation to proceed. The degree of electrode protrusion from the venous catheter is such that the sliding electrode impinges on the material of the grounding electrode of the arterial catheter which is in aligned parallel position directly adjacent to the venous catheter. This circumstance is illustrated by FIG. 26.

Figure 26:
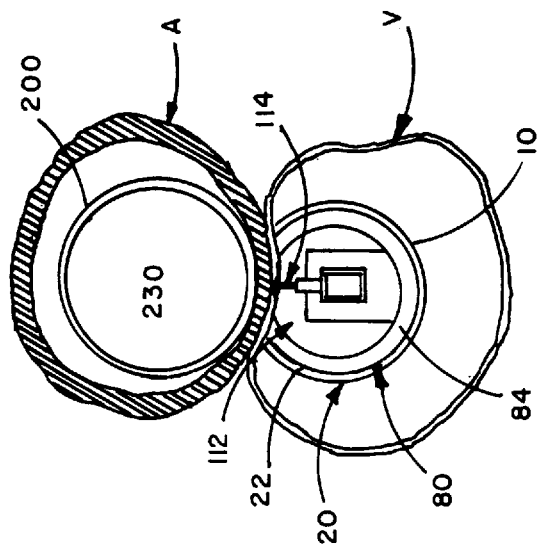
FIG. 26 is a cross-section illustration of the aligned venous catheter and arterial catheter showing the act of perforating vascular walls to generate an arteriovenous fistula.

In this manner, the protruding sliding electrode of the venous catheter can be moved up to 8 mm axially depending on the desired length of the incision; and the grounding electrode of the arterial catheter completes the radiofrequency electrical circuit (as shown by FIG. 26). By completing the radiofrequency electrical circuit at the chosen anatomic site and delivering the appropriate current to the completed circuit, a direct and effective perforation of the venous vascular wall and the arterial vascular wall concurrently can be achieved on-demand.

Simultaneous with the delivery of radiofrequency electrical energy to the completed circuit, a bolus of compressed carbon dioxide gas is introduced into the lumens of both the artery and the immediately adjacent vein. The $CO_2$ gas transiently displaces the blood at the chosen anatomic site during the process of perforating both vascular walls. Since blood is an electrically conductive medium, the $CO_2$ gas displacement increases the current density at the point of contact between the radiofrequency electrode and the vascular wall and facilitates the perforation of both vascular walls concurrently, while minimizing the quantity of tissue destruction that results. Carbon dioxide is extremely soluble and therefore does not result in gas embolism. It has been previously shown (experimentally and clinically) that large volumes of compressed $CO_2$ gas can be introduced intravenously and intraarterially without incurring harmful effects in-vivo.

After the vascular wall perforation process has been satisfactorily completed and the AV fistula created at the chosen anatomic site, the radiofrequency current is disrupted; and the sliding electrode is disengaged and withdrawn into the protective interior of the venous catheter. The venous cutting tool is then withdrawn 2–5 mm proximally relative to the venous cylinder component while holding the arterial catheter steady in its prior position within the artery. This act of withdrawing the venous cutting tool from the cylinder causes the transvascular magnetic attraction to be broken while the arterial catheter is maintained unchanged in its prior aligned position at the perforation site. Radiopaque contrast medium can then be injected into the artery via the internal lumen of the arterial catheter; and the AV fistula assessed fluoroscopically. Evidence of extravasation at the fistula site can therefore be ruled out as well.

The result of this methodology and procedure is the generation of an AV fistula on-demand between closely associated arteries and veins at a carefully chosen and verified vascular anatomical site in-vivo. The radiologist can halt the sequence of steps at any time prior to activating the vascular wall perforation means (the radiofrequency electrode circuitry in this preferred embodiment) without risk or hazard to the patient or the peripheral blood circulation in any substantial manner. Moreover, the methodology allows the radiologist to repeatedly assess, verify, and confirm his choices of anatomical site location; note the alignment and positioning of the arterial catheter as well as the alignment orientation and positioning of the venous catheter; and achieve the proper result and consequence of transvascular magnetic attraction which results in changes in position for one or both of the catheters in-vivo—all which occur prior to engaging the means for physically perforating the vascular walls and generating an aperture between the artery and the adjacently positioned vein.

VI. Illustrative Applications And Usages

A number of intended applications and exemplary usages are briefly described below. Each of these is merely one representative instance of use for the present invention; and many other applications exist presently where the catheter apparatus can be advantageously employed for the benefit of the patient.

A. Hemodialysis Access

A major advantage of the PAVFC technique is the avoidance of a surgical procedure. As stated earlier, renal failure patients have impaired would healing, and an increased incidence of wound infections. In addition, renal failure is associated with modest degrees of immunosuppression. As such, wound infections can lead readily to sepsis and potentially fatal complications. A technique that permits creation of hemodialysis access without necessitating an incision is very attractive. In addition, the procedure would not require an anesthetic and anesthesiologist, or operating room time and personnel, and could therefore be performed at lower cost.

For reasons discussed earlier, a fistula is preferred over a prosthetic arteriovenous shunt. Unfortunately, however, surgical access is often limited to the distal radial artery; and often, there is not a vein of sufficient size in this area. The PAVFC technique allows fistula formation in areas where surgical exposure would be problematic. As such, there are more potential sites available. This allows a more ideal fistula to be created, without the risk of venous kinking.

The PAVFC technique allows evaluation of the juxta arterial venous system of the entire extremity by intravascular ultrasound to identify the most favorable anatomic site and provides accurate assessment of venous diameter. Veins on which surgical anastomosis would be difficult due to small size or thin walls are easily addressed and utilized by the PAVFC. More importantly, the vessels are not dissected out or manipulated, preserving the tenuous vaso vasorum, which will improve patency.

Potential problems with this technique are few, and relate primarily to the risk of hemorrhage. If an anatomically favorable site is selected, this risk will be quite small. In the event of hemorrhage, an expanding hematoma in the arm is clinically obvious, and is readily controlled with the direct pressure using a blood pressure cuff or manual compression. It may prove necessary to surgically explore patients in whom compression proves inadequate. The risk of using intravenous contrast to facilitate fluoroscopic visualization of arm venous anatomy is small, as is the risk of intraarterial contrasts to assist adequacy of the AV fistula post-procedure.

B. Portal Venous Hypertension And Veno-Venous Fistulae

Portal venous hypertension develops as a complication of end stage cirrhosis, and other forms of liver disease. The portal veins drain from the intestine to the liver. The blood is filtered through the liver before entering the systemic venous system, and returning to the heart. When the liver becomes badly diseased, resistance to portal venous flow increases. The filter mechanism becomes "clogged". As a result, the pressure in the portal venous systemic increases, which results in massive dilation of the naturally occurring portal-systemic venous connections.

One such area of portal-systemic venous connection is at the gastroesophageal junction (near the top of the stomach). These thin walled, massively dilated veins often rupture spontaneously, resulting in exsanguinating upper gastrointestinal hemorrhage, which is frequently lethal. Surgical therapy is directed at lowering the portal venous pressure by creating a shunt between the portal vein or it's major branches, and the systemic venous system, usually the inferior vena cava. The operation is effective in lowering portal venous pressure in most patients, and usually prevents additional bleeding episodes. The procedure is, however, quite risky. Patients with advanced liver disease tolerate surgery poorly, with reported operative mortality of 10%, 50%, and 80% for portalcaval bypass in patients with early, intermediate, and late stage liver failure, respectively.

Percutaneous creation of portal-systemic connection has been performed at many institutions with some success. The current technique, however, does not permit identification of closely adjacent portal and systemic veins, does not utilize magnetic attraction to bring the adjacent veins into close proximity, and does not utilize radiofrequency current, laser energy, or static discharge to create the connection. Each of these modification of the current percutaneous technique represents a major technical advance, and will result in a larger portosystemic connection, and better portal venous decompression. As such, the PAVFC catheter and technique is extremely useful in this field. One catheter is introduced via the femoral or jugular vein and is advanced into the inferior vena cava to the level of the portal vein. The second catheter is introduced into the portal venous system by way of percutaneous transhepatic puncture or by transjugular-hepatic approach. Proximity of the two catheters is achieved with intravascular ultrasound and fluoroscopy, as described for dialysis access. A variety of veno-venous fistulae can be generated in this manner.

C. Creation of Graft Material

The PAVFC catheters and technique are useful in the creation of suitable conduit, or graft material, in anticipation of subsequent Minimally Invasive Coronary Artery Bypass Grafting (MICABG). MICABG is a rapidly evolving technique that allows blocked coronary arteries to be bypassed without necessitating cardiopulmonary bypass or cardiac arrest.

Traditionally, when a patient develops critical narrowing of the coronary arteries not amenable to medical management or angioplasty, a conventional coronary artery bypass is performed. The patient's chest is opened, and the heart attached to the heart lung machine by way of large cannula inserted in the aorta and right atrium. The heart lung machine pumps and oxygenates the blood, enabling the surgeon to temporarily arrest the heart by mechanical and pharmacological means, without interrupting blood flow to the brain, kidneys, and other vital organs. A clamp is placed on the ascending aorta, which deprives the heart of blood and results in cessation of cardiac activity. The clamp also allows the proximal ends of segments of saphenous vein, harvested from the patient's leg, to be attached to the aorta in a blood free environment. The distal ends of the vein grafts are attached to the coronary arteries beyond the areas of critical narrowing. Some coronary arteries are bypassed with the left or right internal mammary arteries. Long term patency of mammary grafts is much better than that seen with vein grafts. In addition, no proximal anastomosis is necessary as the mammary arteries are already branches of the arterial tree, and therefore carry arterial flow despite leaving the proximal artery in situ. The crossclamp is then removed, and blood flow restored to the heart.

MICABG is a new method of surgical revascularization that has the potential of being less risky than conventional bypass. Most, if not all, of the morbidity associated with conventional coronary artery bypass is related to cardiopulmonary bypass and temporary cardiac arrest. The MICABG technique allows the surgeon to graft the coronary arteries without necessitating these maneuvers. MICABG is not without limitations, however. With this technique, the heart continues to beat, and eject blood at high pressure and flow through the ascending aorta. As such, it is not currently possible to attach vein grafts to the aorta. All grafting must therefore be performed with arteries as they do not require proximal anastomosis. Thoracic arteries suitable for use as grafts are, unfortunately, in short supply. Only the left and right internal mammaries are of adequate diameter and length to be of use. The gastroepiploic artery can be used for grafting, but requires a laparotomy for harvest, and is technically more demanding.

The PAVFC catheters and technique are of use in patients undergoing MICABG. Each of the 12 paired ribs has closely associated with it a neurovascular bundle. This bundle contains a sensory nerve, an artery, and a closely associated vein. The artery measures only 1 to 1.5 mm in diameter, and as such, is of inadequate diameter to be used as a graft. If, however, a fistula is created between the distal intercostal artery and vein, both thin walled vessels will dilate with time. This dilation of intercostal arteries from increased flow is observed clinically in patients with coarctation of the aorta. Patients electively scheduled to undergo MICABG could have distal intercostal fistulas created in one or more of the larger intercostal arteries with the PAVFC technique, approximately, 6 weeks prior to anticipated heart surgery.

What we claim is:

1. A catheterization method for generating a fistula on-demand between closely associated blood vessels at a chosen anatomic site in-vivo, said catheterization method comprising the steps of:

procuring at least one catheter suitable for percutaneous introduction into and extension through a blood vessel in-vivo to a chosen anatomic site, said catheter being comprised of
   (a) a tube having a fixed axial length, a discrete proximal end, a discrete distal end, and at least one internal lumen of predetermined volume,
   (b) a distal end tip adapted for intravascular guidance of said tube through a blood vessel in-vivo to a chosen anatomic site,
   (c) magnet means positioned at said discrete distal end and set in axial alignment with said distal end tip of said tube, said magnet means having sufficient magnetic force to cause an intravascular adjustment in position for said catheter when in proximity with a source of magnetic attraction disposed within a closely associated blood vessel in-vivo,
   (d) vascular wall perforation means positioned at said discrete distal end adjacent to said magnet means and set in axial alignment with said distal end tip of said tube, said vascular wall perforation means becoming intravascularly adjusted in position via the magnetic force of said magnet means when in proximity with a source of magnetic attraction disposed within a closely associated blood vessel in-vivo,
   (e) means for activating said vascular wall perforation means of said catheter on-demand wherein said vascular wall perforation means perforates a chosen anatomic site between closely associated blood vessels;

percutaneously introducing said catheter into a first blood vessel and extending said catheter intravascularly to a chosen site adjacent to a closely associated second blood vessel;

percutaneously introducing a source of magnetic attraction into a closely associated second blood vessel and extending said source of magnetic attraction intravascularly to a chosen anatomic site in proximity to said extended catheter;

permitting a transvascular magnetic attraction to occur between said magnet means of said extended catheter in the first blood vessel and said source of magnetic attraction in the closely associated second blood vessel whereby said vascular wall perforation means of said catheter in the first blood vessel comes into transvascular alignment with the closely associated second blood vessel at the chosen anatomic site; and then activating said vascular wall perforation means of said catheter on-demand wherein said vascular wall perforation means perforate of said catheter the vascular walls of said closely associated blood vessels concurrently at the chosen anatomic site to generate a fistula in-vivo.

2. A catheterization method for generating an arteriovenous fistula on-demand between a closely associated artery and vein at a chosen anatomic site in-vivo, said catheterization method comprising the steps of:

procuring a first catheter suitable for percutaneous introduction into and extension through a vein in-vivo to a chosen anatomic site, said first catheter being comprised of
(a) a first tube having a fixed axial length, a discrete proximal end, a discrete distal end, and at least one internal lumen of predetermined volume,
(b) a distal end tip adapted for intravascular guidance of said first tube through a vein in-vivo to a chosen anatomic site,
(c) first magnet means positioned at said discrete distal end and set in axial alignment with said distal end tip of said first tube, said first magnet means having sufficient magnetic force to cause an intravascular adjustment in position for said first catheter when in proximity with a source of magnetic attraction in-vivo, and
(d) a first component of vascular wall perforation means positioned at said discrete distal end adjacent to said first magnet means and set in axial alignment with said distal end tip of said first tube, said first component of vascular wall perforation means becoming intravascularly adjusted in position via the magnetic force of said first magnetic means of said first catheter in-vivo,
(e) means for activating said first component of vascular wall perforation means of said first catheter on-demand wherein said vascular wall perforation means perforates a chosen anatomic site to generate a fistula in-vivo;

percutaneously introducing said first catheter into a vein and extending said first catheter intravascularly to a chosen anatomic site adjacent to a closely associated artery;

procuring a second catheter suitable for percutaneous introduction into and extension through an artery in-vivo to a chosen anatomic site, said second catheter being comprised of
(a) a second tube having a fixed axial length, a discrete proximal end, a discrete distal end, and at least one internal lumen of predetermined volume,
(b) a distal end tip adapted for intravascular guidance of said second tube through an artery in-vivo to a chosen anatomic site,
(c) second magnet means positioned at said discrete distal end and set in axial alignment with said distal end tip of said second tube, said second magnet means having sufficient magnetic force to cause an intravascular adjustment in position for said second catheter when in proximity with said first magnetic means of said first catheter in-vivo,
(d) a second component of vascular wall abutment means positioned at said discrete distal end adjacent to said second magnet means and set in axial alignment with said distal end tip of said second tube, said second component of vascular wall perforation means becoming intravascularly adjusted in position via the magnetic force of said second magnet means of said second catheter in-vivo;

percutaneously introducing said second catheter into an artery and extending said second catheter intravascularly to a chosen anatomic site in proximity to said first catheter in to a closely associated vein;

permitting a transvascular magnetic attraction to occur between said first magnetic means of said extended first catheter in the vein and said second magnetic means of said extended second catheter in the closely associated artery whereby said first component of vascular wall perforation means of said first catheter lying within the vein comes into transvascular alignment with said second component of vascular wall abutment means of said second catheter lying within the artery; and then activating said first component of vascular wall perforation means of said first catheter on-demand wherein said vascular wall perforation means perforate the vascular walls of said vein and closely associated artery concurrently at the chosen anatomic site to generate an arteriovenous fistula in-vivo.

* * * * *